US010548708B2

(12) United States Patent
Bertolino et al.

(10) Patent No.: US 10,548,708 B2
(45) Date of Patent: Feb. 4, 2020

(54) ANTI-MIGRATION MICROPATTERNED STENT COATING

(71) Applicant: BOSTON SCIENTIFIC SCIMED, INC., Maple Grove, MN (US)

(72) Inventors: William Bertolino, Framingham, MA (US); Laura Elizabeth Firstenberg, Boston, MA (US); Claire M. McLeod, Philadelphia, PA (US); Andrea Lai, Deer Park, IL (US); Sandra Lam, Rancho Palos Verdes, CA (US); Shannon Taylor, St. Simons Island, GA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/355,529

(22) Filed: Nov. 18, 2016

(65) Prior Publication Data

US 2017/0065398 A1 Mar. 9, 2017

Related U.S. Application Data

(63) Continuation of application No. 14/459,084, filed on Aug. 13, 2014, now Pat. No. 9,526,640.

(Continued)

(51) Int. Cl.
*A61F 2/82* (2013.01)
*A61F 2/04* (2013.01)
(Continued)

(52) U.S. Cl.
CPC ............... *A61F 2/04* (2013.01); *A61F 2/848* (2013.01); *A61F 2/90* (2013.01); *B29C 45/372* (2013.01);
(Continued)

(58) Field of Classification Search
CPC .... A61F 2/82; A61F 2/848; A61F 2250/0056; A61F 2/0077; A61F 2002/072;
(Continued)

(56) References Cited

U.S. PATENT DOCUMENTS

| 6,911,035 B1 | 6/2005 | Blomme |
| 8,267,992 B2 | 9/2012 | Atanasoska |

(Continued)

FOREIGN PATENT DOCUMENTS

| JP | 2011509758 A | 3/2011 |
| JP | 2012065825 A | 4/2012 |

OTHER PUBLICATIONS

Conigliaro et al., "Polyflex stents for malignant oesophageal and oesophagogastric stricture: a prospective, multicentric study," European Journal of Gastroenterology & Hepatology, vol. 19(3): 195-203, 9 pages, Mar. 2007.

(Continued)

*Primary Examiner* — Seema Mathew
(74) *Attorney, Agent, or Firm* — Seager, Tufte & Wickhem, LLP

(57) ABSTRACT

An endoprosthesis has an expanded state and a contracted state, the endoprosthesis includes a stent having an inner surface defining a lumen, having an outer surface, and defining a plurality of apertures through the outer surface, wherein the apertures are arranged in a micropattern; and a coating (e.g., polymeric coating) attached to the outer surface of the stent. The coating includes a base and a tissue engagement portion including a second surface facing outwardly from the stent, the tissue engagement portion including a structure that defines a plurality of holes extending inwardly from the second surface toward the base. The holes are arranged in a micropattern. When the endoprosthesis is expanded to the expanded state in a lumen defined by a (Continued)

vessel wall, the structure applies a force that may reduce stent migration by creating an interlock between the vessel wall and the endoprosthesis.

13 Claims, 13 Drawing Sheets

Related U.S. Application Data

(60) Provisional application No. 61/867,074, filed on Aug. 18, 2013.

(51) Int. Cl.

| | | |
|---|---|---|
| *A61F 2/848* | (2013.01) | |
| *A61F 2/90* | (2013.01) | |
| *B29C 65/48* | (2006.01) | |
| *B29C 65/00* | (2006.01) | |
| *B29C 45/37* | (2006.01) | |
| *B29C 53/58* | (2006.01) | |
| *B29D 23/00* | (2006.01) | |
| *B29K 101/00* | (2006.01) | |
| *B29L 23/00* | (2006.01) | |
| *B29L 31/00* | (2006.01) | |
| *B29L 16/00* | (2006.01) | |
| *B29C 41/14* | (2006.01) | |
| *B29C 33/42* | (2006.01) | |
| *B29C 39/02* | (2006.01) | |
| *B29C 39/10* | (2006.01) | |
| *B29C 41/20* | (2006.01) | |

(52) U.S. Cl.
CPC ........ *B29C 65/48* (2013.01); *B29C 66/52272* (2013.01); *B29C 66/742* (2013.01); *A61F 2002/044* (2013.01); *A61F 2002/8483* (2013.01); *A61F 2002/8486* (2013.01); *A61F 2220/005* (2013.01); *A61F 2220/0016* (2013.01); *A61F 2240/001* (2013.01); *A61F 2250/0059* (2013.01); *B29C 33/42* (2013.01); *B29C 33/424* (2013.01); *B29C 39/026* (2013.01); *B29C 39/10* (2013.01); *B29C 41/14* (2013.01); *B29C 41/20* (2013.01); *B29C 53/587* (2013.01); *B29C 66/1122* (2013.01); *B29C 66/5326* (2013.01); *B29D 23/00* (2013.01); *B29D 23/001* (2013.01); *B29K 2101/00* (2013.01); *B29L 2016/00* (2013.01); *B29L 2023/00* (2013.01); *B29L 2031/7532* (2013.01); *B29L 2031/7534* (2013.01)

(58) Field of Classification Search
CPC ...... A61F 2/07; A61F 2/90; A61F 2250/0051; A61F 2250/0068; A61L 2400/12; A61L 31/14; B29C 33/42
See application file for complete search history.

(56) References Cited

U.S. PATENT DOCUMENTS

| | | |
|---|---|---|
| 2002/0082685 A1 | 6/2002 | Sirhan et al. |
| 2002/0123790 A1 | 9/2002 | White et al. |
| 2003/0009213 A1 | 1/2003 | Yang |
| 2005/0203613 A1 | 9/2005 | Arney et al. |
| 2005/0208100 A1 | 9/2005 | Weber et al. |
| 2005/0255230 A1 | 11/2005 | Clerc et al. |
| 2005/0273121 A1 | 12/2005 | Sato et al. |
| 2006/0069425 A1 | 3/2006 | Hillis et al. |
| 2006/0085062 A1* | 4/2006 | Lee ............... A61F 2/90 623/1.39 |
| 2006/0136051 A1* | 6/2006 | Furst ............. A61F 2/91 623/1.42 |
| 2007/0224235 A1* | 9/2007 | Tenney ........... A61F 2/30767 424/423 |
| 2008/0086113 A1* | 4/2008 | Tenney ........... A61L 27/54 604/892.1 |
| 2008/0140182 A1* | 6/2008 | Scheller .......... A61F 2/07 623/1.17 |
| 2008/0195189 A1* | 8/2008 | Asgari ............ A61F 2/82 623/1.2 |
| 2008/0319540 A1* | 12/2008 | Jordan ............ A61L 31/14 623/1.49 |
| 2009/0081271 A1* | 3/2009 | Clarke ............ A61F 2/00 424/423 |
| 2009/0187240 A1 | 7/2009 | Clerc et al. |
| 2010/0076555 A1 | 3/2010 | Marten et al. |
| 2010/0256064 A1 | 10/2010 | Woolfson et al. |
| 2011/0172760 A1* | 7/2011 | Anderson ........ A61B 17/0057 623/1.15 |
| 2013/0046371 A1 | 2/2013 | Greenberg et al. |
| 2013/0110255 A1 | 5/2013 | Picha et al. |
| 2013/0184808 A1 | 7/2013 | Hall et al. |
| 2013/0218262 A1 | 8/2013 | Ishii et al. |
| 2013/0231753 A1 | 9/2013 | Liddy et al. |
| 2014/0067046 A1 | 3/2014 | Perry et al. |
| 2014/0148897 A1 | 5/2014 | Matheny |
| 2014/0277442 A1 | 9/2014 | Seddon et al. |
| 2014/0277443 A1 | 9/2014 | Fleury et al. |
| 2014/0277561 A1 | 9/2014 | Jordan |
| 2015/0282955 A1 | 10/2015 | Guler et al. |
| 2016/0000553 A1 | 1/2016 | Levi et al. |
| 2016/0128852 A1* | 5/2016 | Leanna ........... A61F 2/89 623/9 |
| 2016/0158040 A1* | 6/2016 | Zupkofska ....... A61F 2/82 623/23.7 |
| 2019/0076274 A1* | 3/2019 | Hingston ......... A61L 31/005 |

OTHER PUBLICATIONS

Conio et al., "A Randomized Perspective Comparison of Self-Expandable Plastic Stents and Partially Covered Self-Expandable Metal Stents in the Palliation of Malignant Esophageal Dysphagia," American Journal of Gastroenterology, vol. 102(12): 2667-2677, 11 pages, Dec. 2007.

Schembre, "Advances in esophageal stenting: the evolution of fully covered stents for malignant and benign disease," Advanced Therapy, vol. 27(7): 412-425, 13 pages, Jul. 2010.

Sharma et al., "Role of esophageal stents in benign and malignant diseases," American Journal of Gastroenterology, vol. 105(2): 258-273, 16 pages, Dec. 2009.

Shim, "Esophageal stenting in unusual situations," Endoscopy, vol. 35:14-18, 5 pages, 2003.

Throm Quilan et al., "Combining dynamic stretch and tunable stiffness to probe cell mechanobiology in vitro," PLoS one, vol. 6(8): e23272, 9 pages, Aug. 2011.

Van Broeckel et al., "A new partially covered metal stent for palliation of malignant dysphagia: a prospective follow-up study," Gastrointestinal Endoscopy, vol. 72(6): 1269-1273, 5 pages, Dec. 2010.

\* cited by examiner

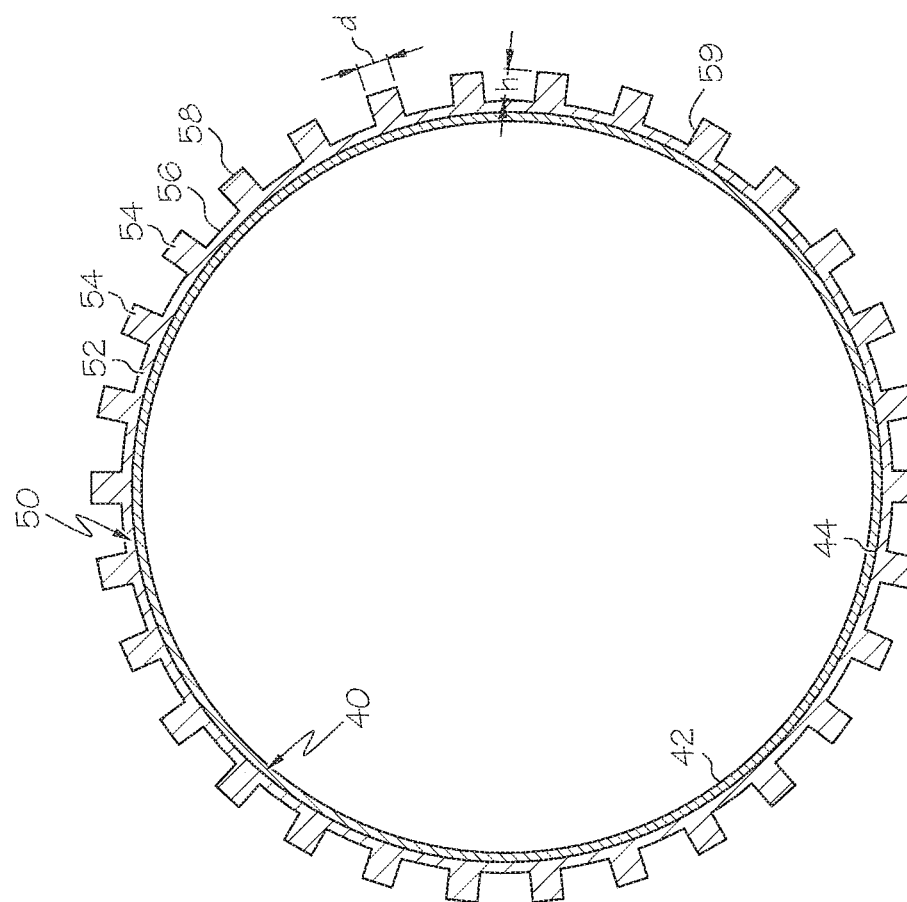

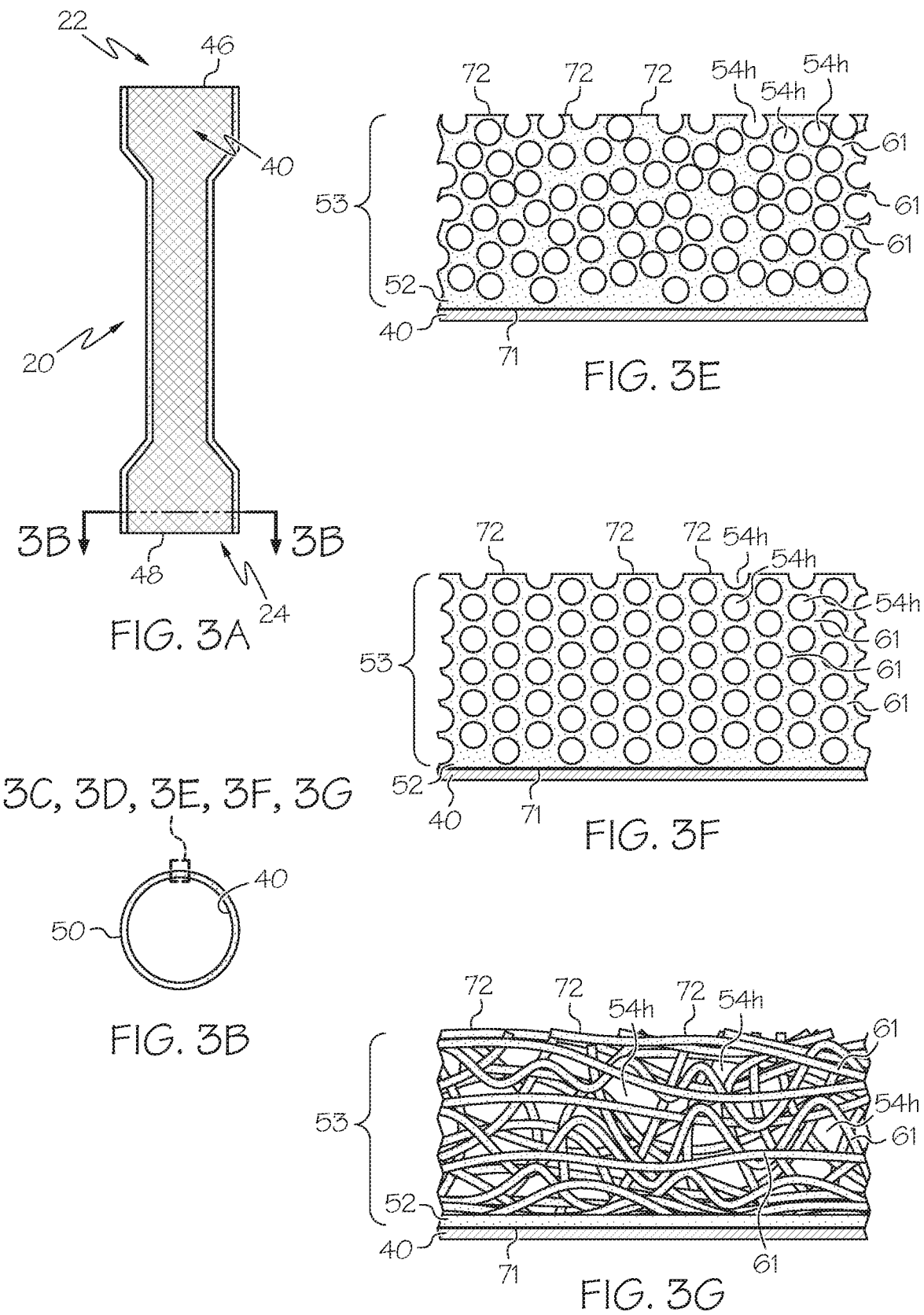

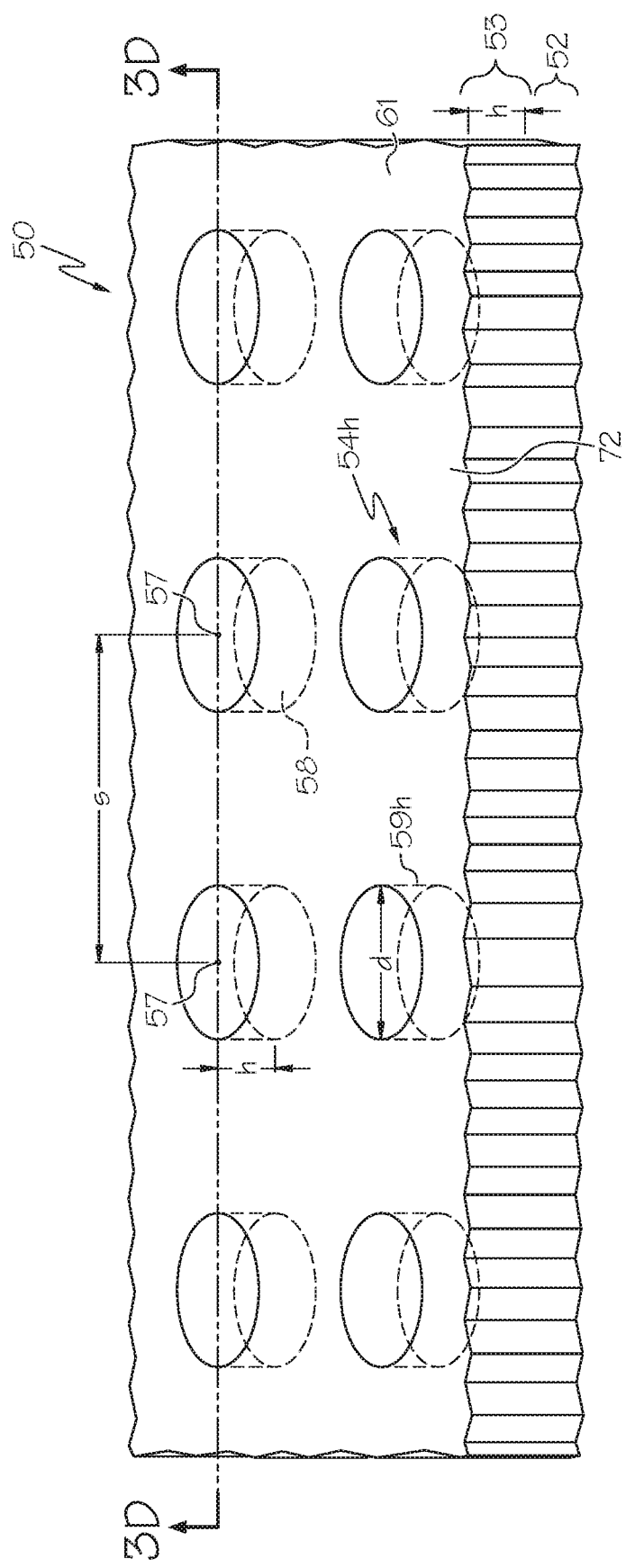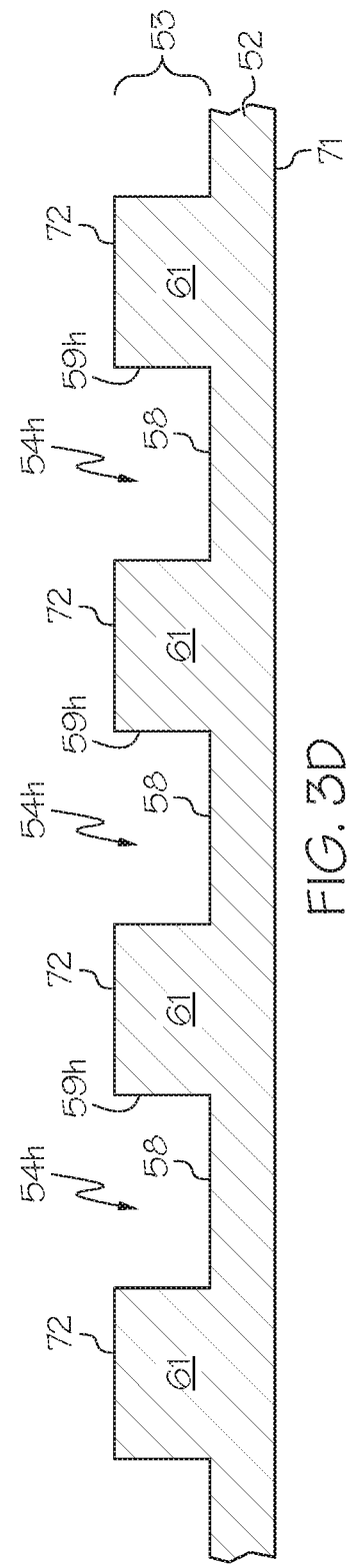
FIG. 3C
FIG. 3D

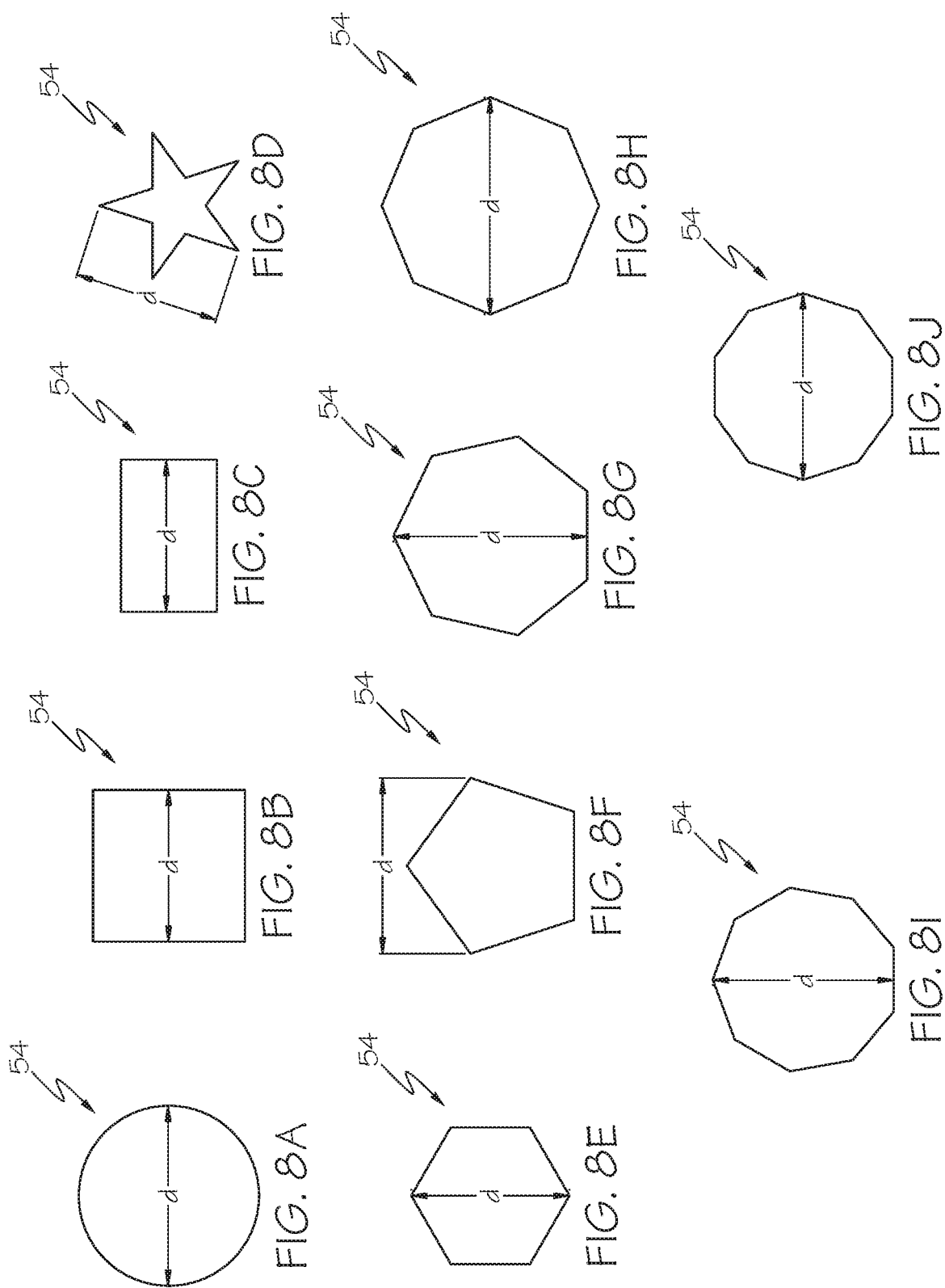

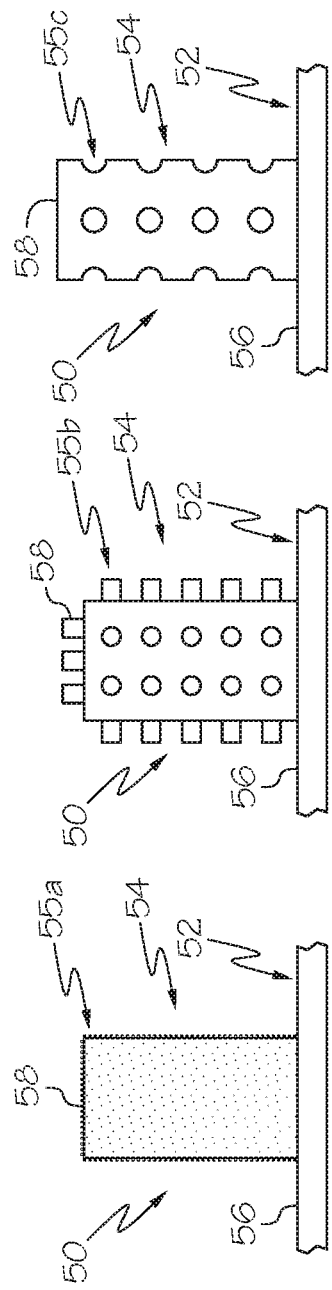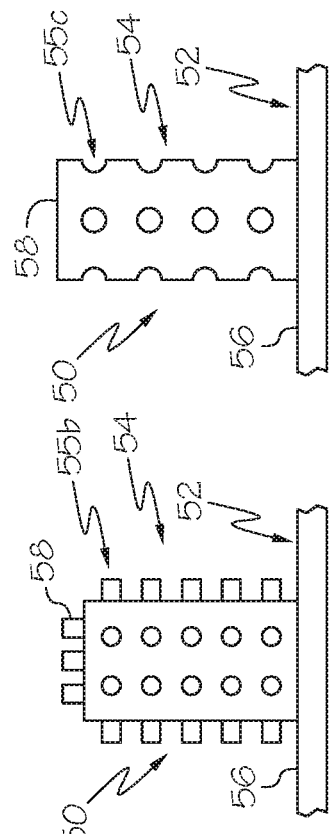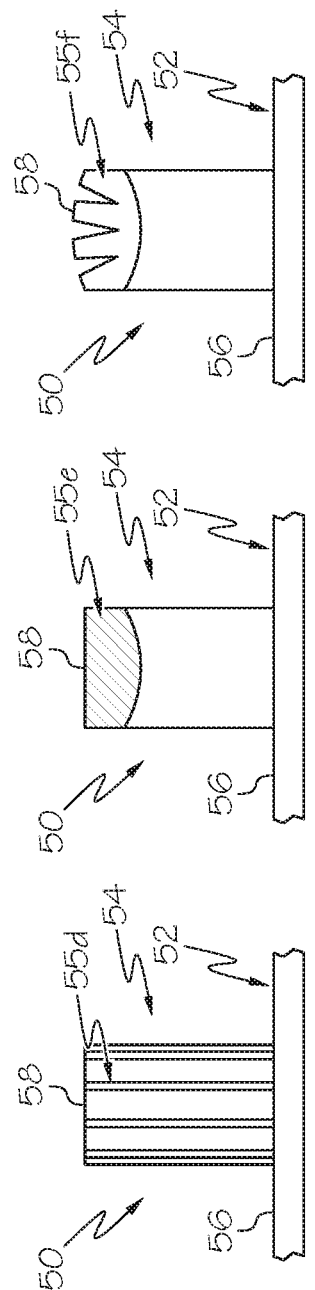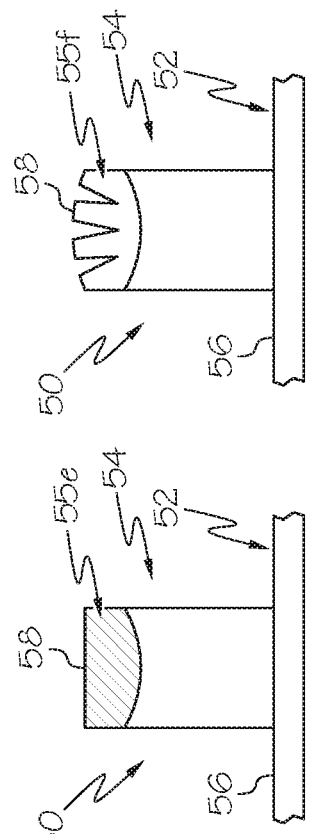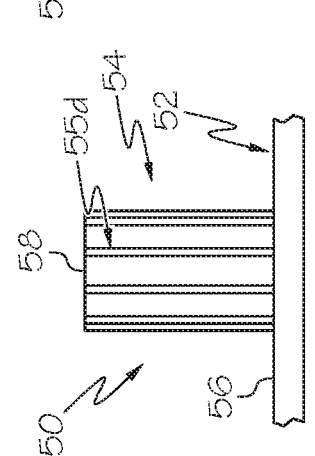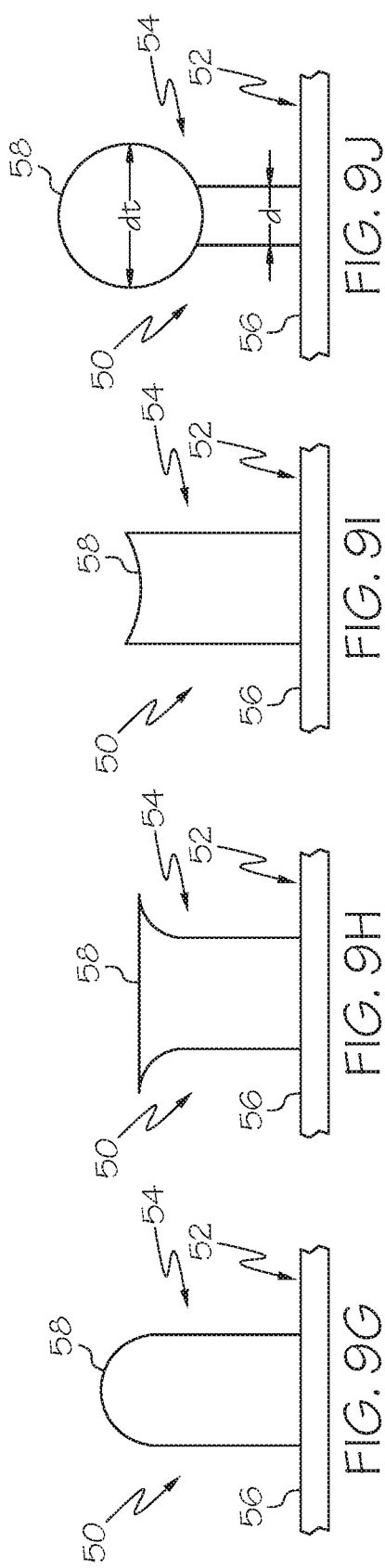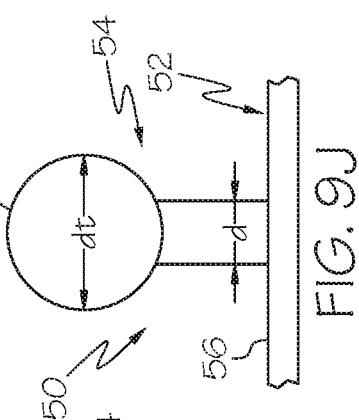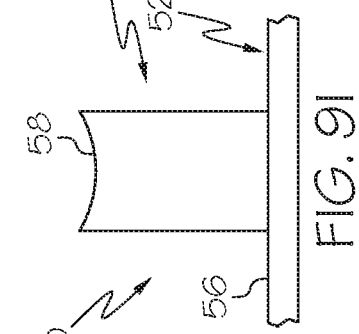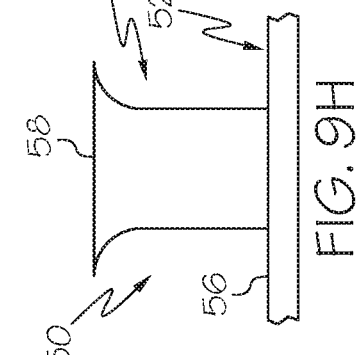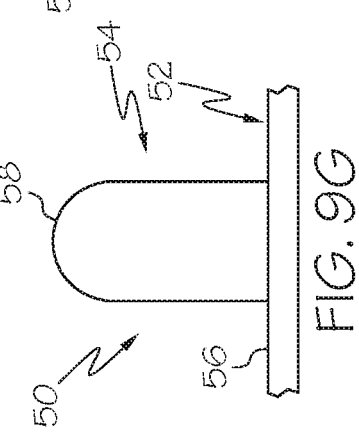

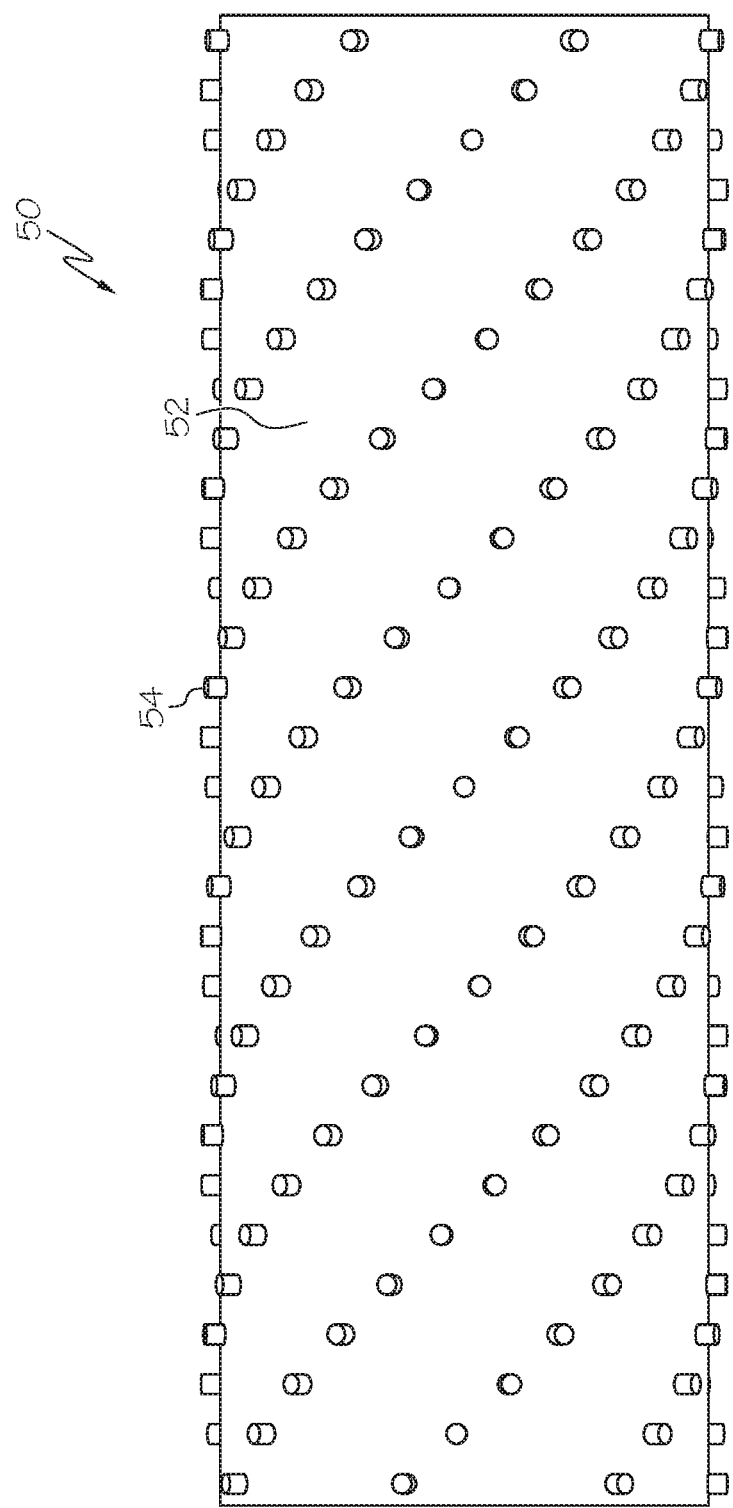

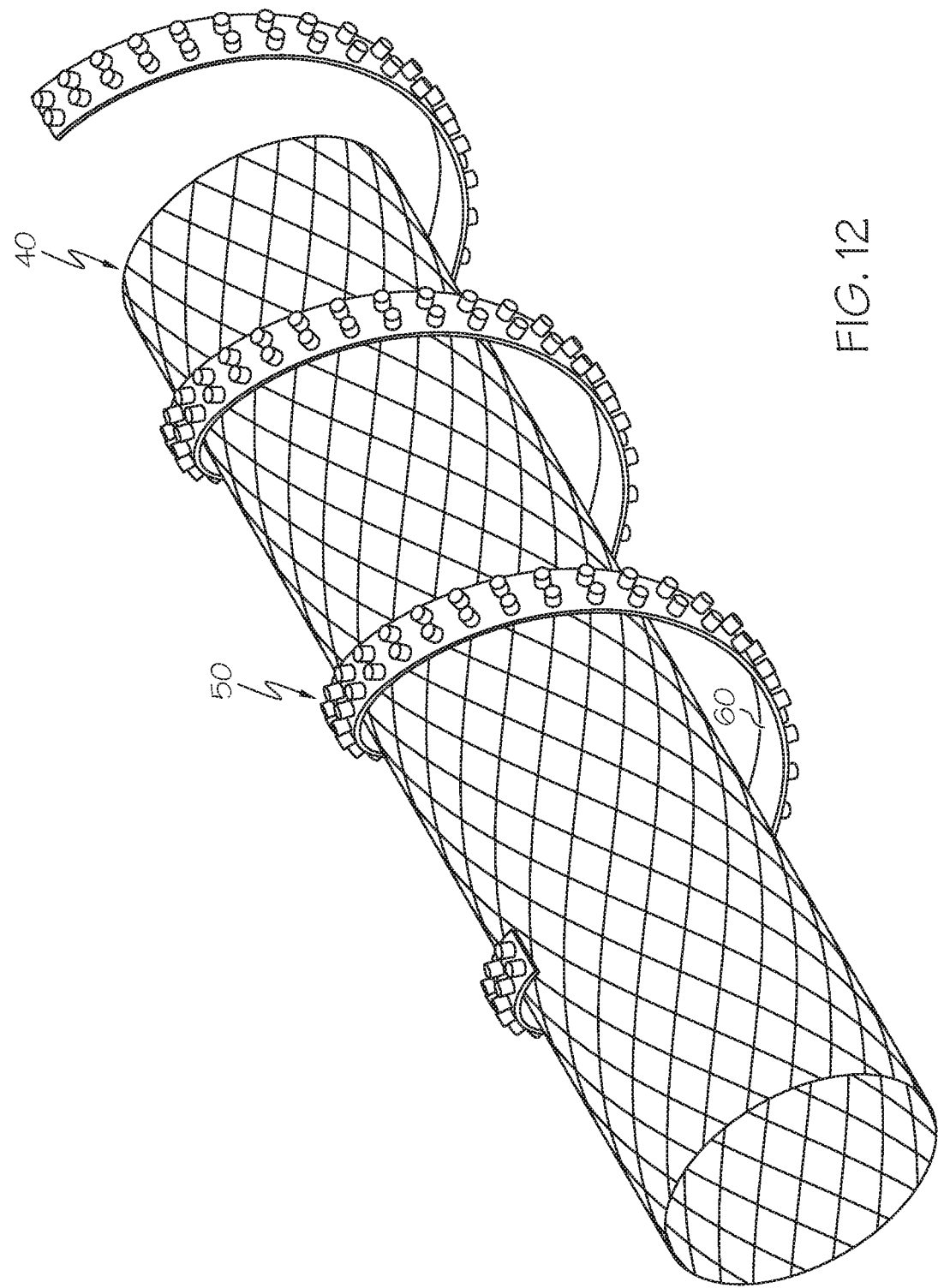

ANTI-MIGRATION MICROPATTERNED STENT COATING

CROSS REFERENCE TO RELATED APPLICATIONS

This application is a continuation of U.S. application Ser. No. 14/459,084, filed Aug. 13, 2014, which claims the benefit of and priority to U.S. Provisional Application No. 61/867,074, filed Aug. 18, 2013, which is incorporated herein by reference in its entirety, and incorporates by reference the following applications, each in its entirety: U.S. Provisional Patent Application No. 61/621,219, filed Apr. 6, 2012, U.S. patent application Ser. No. 13/857,998, filed Apr. 6, 2013, and U.S. Provisional Patent Application No. 61/798,685, filed Mar. 15, 2013.

BACKGROUND OF THE DISCLOSURE

A stent is a medical device introduced into a body lumen and is well known in the art. A stent may be delivered in an unexpanded state to a desired location in a bodily lumen and then expanded by an internal radial force. Stents, grafts, stent-grafts, vena cava filters, expandable frameworks, and similar implantable medical devices, collectively referred to hereinafter as stents, have included radially expandable endoprostheses, which have been used as intravascular implants capable of being implanted transluminally.

Esophageal stents have been used to treat patients suffering from a range of malignant and non-malignant diseases. Most commonly, esophageal stents have been associated with the treatment (e.g., palliative) of esophageal cancers. Esophageal stents have also been used to reduce symptoms resulting from non-esophageal tumors that grow to obstruct the esophagus and to treat benign esophageal disorders, including but not limited to refractory strictures, fistulas and perforations. In each of these cases, esophageal stents may provide mechanical support to the esophageal wall, may maintain luminal patency, and/or may alleviate symptoms including pain, choking sensations, and severe difficulty swallowing. Because of the structure of the esophagus and conditions such as peristalsis, esophageal stents have been prone to stent migration. When migration occurs, the patient may experience the return of symptoms and reintervention (e.g., stent repositioning, stent removal) may be required.

One way to reduce the risk of stent migration has been to expose bare metal portions of the stent to esophageal tissue. The open, braided structure of the stent may provide a scaffold that promotes tissue ingrowth into the stent. This tissue ingrowth may aid anchoring the stent in place and may reduce the risk of migration.

In some cases, however, tissue ingrowth has been known to lead to reocclusion of the esophagus, for example, in patients receiving a stent to treat malignant growth. In addition, esophageal stents anchored by tissue ingrowth cannot be moved or removed without an invasive procedure (e.g., causing trauma to a patient). To reduce tissue ingrowth, stents have been covered with a coating (e.g., made of a polymer, etc.) to create a physical barrier between the lumen and the esophageal wall. However, in some circumstance, such stents can have an unacceptable occurrence of migration, as compared to bare metal counterparts.

Some stents are fully degradable and have been designed to be present in a body lumen for a predetermined period of time following delivery and deployment after which the stent degrades. However, these stents do not have control over lumen reocclusion built into its design.

Another way to reduce the risk of stent migration has been to use a flared stent (e.g., in the esophagus). However, stents having flares can have an unacceptable occurrence of migration. Stents have been known to include flares (e.g., flared ends), which include many shapes and both covered and uncovered varieties. Flares have been used to anchor a stent at an implantation site (e.g., in the esophagus) and have been shown to reduce migration. However, further decreases in migration rates are desired.

In one or more applications, removable stents are desired, for example, in applications for treating benign disorders. Some applications of stents include use as a bridge to treatment and less of a palliative measure, due in part to improvements in some cancer therapies and other methods of treating malignant growths. However, efforts to improve removability have been at odds with at least some measures taken to reduce risk of stent migration. Improved stents that reduce trauma during stent removal and improve stent adhesion to the body lumen (e.g., esophageal wall) are desired.

Some fully covered stents have additionally included a second woven-metal layer external to the fully covered stent that may allow tissue ingrowth without allowing tissue overgrowth to occlude the body lumen (e.g., esophagus, etc.). However, the additional scaffolding that allows for tissue ingrowth may undesirably increase the stent profile.

Improved stents with, for example, improved resistance to migration, improved stent adhesion to the esophageal wall, and/or improved removability are desired. Some tracheal stents have incorporated bumps or other surface features into the stent itself or have included a plurality of surface protrusions on the outer surface of the stent.

Without limiting the scope of the present disclosure, a brief summary of some of the claimed embodiments is set forth below. Additional details of the summarized embodiments of the present disclosure and/or additional embodiments of the present disclosure may be found in the Detailed Description of the Disclosure below. A brief abstract of the technical disclosure in the specification is also provided. The abstract is not intended to be used for interpreting the scope of the claims.

BRIEF SUMMARY OF THE DISCLOSURE

The present disclosure provides an endoprosthesis where a preferably polymeric coating has a number of surface features such as protrusions or holes that are arranged in a micropattern. As used herein, a micropattern may include a regular or irregular array of micro-scale features (e.g., protrusions such as micropillars, voids such as holes). Generally, micro-scale feature means a feature having a dimension (e.g., length, width, or height) in a range of from about 1 micrometer to about 999 micrometers. Herein, unless the context indicates otherwise, micro-scale features are referred to as micropillars (e.g., extending from a base) or holes. In one or more embodiments disclosed herein, a biointeractive micropatterned stent coating may provide a solution for maintaining luminal patency while including potential for removability and reducing migration.

Herein, micro-scale features are referred to as micropillars (e.g., extending from a base) and holes (e.g., microholes, extending within a tissue engagement portion). It should be noted that, unless the context indicates otherwise, the description of micropillar shapes, dimensions, and arrangement applies equally to holes (e.g., microholes).

In at least one embodiment, an endoprosthesis, having an expanded state and a contracted state, includes a stent with a polymeric coating attached (e.g., adhered, etc.) to an outer surface of the stent. The stent has an inner surface defining a lumen. The stent has an outer surface and a stent thickness defined between the inner surface and outer surface. The stent defines a plurality of apertures extending through the stent thickness, wherein the apertures are arranged in a macropattern. In at least one embodiment, the stent is a flared stent.

As used herein, a "macropattern" of apertures (e.g., stent apertures) refers to a regular or irregular pattern of apertures wherein the shortest center-to-center distance (i.e., the distance between the geometric centers) of adjacent apertures (i.e., apertures that share a side) is greater than 1000 micrometers. The shortest center-to-center distance in a macropattern of stent apertures is measured when the stent is in a fully expanded state. For example, in a braided stent that defines a plurality of four-sided apertures (e.g., extending from an inner surface of the stent to an outer surface of the stent) arranged in a macropattern, the distance between geometric centers of two apertures that share one side is greater than 1000 micrometers when the stent is in its expanded state. In a regular pattern of apertures, each of the two geometric centers are equidistant from the side shared by the adjacent apertures. In an irregular pattern of apertures, the two geometric centers are not equidistant from the side shared by the adjacent apertures.

The polymeric coating includes a base and a tissue engagement portion. The base includes a first surface (e.g., attached to the outer surface of the stent). The tissue engagement portion includes a second surface facing outwardly from the stent (e.g., in a direction opposite of the first surface). The tissue engagement portion includes a structure that defines a plurality of holes (e.g., microholes, etc.) extending inwardly from the second surface toward the base. In at least one embodiment, the holes are arranged in a micropattern. In one or more embodiments, the base and the stent are coterminous. In one or more embodiments, the base covers the apertures of the stent. When the endoprosthesis is expanded to the expanded state in a lumen defined by a vessel wall, the structure defining the plurality of holes applies a force that creates an interlock between the vessel wall and the endoprosthesis.

In one or more embodiments, the polymeric coating may include a plurality of protrusions (e.g., micropillars) extending from the base (e.g., outwardly from the stent). In one or more embodiments, the protrusions may be arranged in a micropattern (e.g., of micropillars).

Although not wishing to be bound by theory, tissue may engage and/or interlock a micropatterned coating via one or more mechanisms. For example, tissue may interlock with a micropatterned coating having one or more micropillars by growing around and/or between the one or more micropillars. In at least one embodiment, a tissue ingrowth mechanism may result in tissue engaging and/or interlocking with a micropatterned coating having a structure defining one or more holes (e.g., voids, negative spaces, etc.) or networks of connected holes, wherein tissue and/or cell ingrowth occurs within the holes. In one or more embodiments, a chemical bond mechanism may be formed between a tissue in contact with a micropatterned coating that may include, for example, a mucoadhesive gel. In one or more embodiments, engagement of tissue with a micropattern having an appropriate geometry may be by proximity attraction by van der Waals bonding. Herein, "interlock" means to engage tissue (e.g., by a microstructure having micropillars and/or microholes, etc.) via any of the mechanisms (e.g., tissue ingrowth, chemical bond, proximity attraction, etc.) described herein or otherwise known to one of skill in the art.

The micropattern is specifically designed for a particular tissue in order to effectively interlock the stent with the tissue. In at least one embodiment, the micropattern is present along at least a portion of the endoprosthesis. In at least one embodiment, the holes of the micropattern can be uniform or the micropattern can be formed of holes having a first configuration and holes having at least a second configuration.

The shape of at least some of the plurality of holes may be selected from a group including cylinders, rectangular prisms, polygonal prisms, spheres, spheroids, ellipsoids, and similar shapes. In at least one embodiment, the holes of the micropattern are cylindrical microholes, each cylindrical microhole having a diameter and a height, wherein the diameter of each cylindrical microhole is equal to its height. In at least one embodiment, the cylindrical microhole has a lateral surface, wherein the lateral surface of the cylindrical microhole is separated from the lateral surfaces of an adjacent microhole by a distance greater than the diameter of the cylindrical microhole. In at least one embodiment, the micropattern is a grid pattern.

In at least one embodiment, each hole of the micropattern has a first dimension and a second dimension, wherein the first dimension is between about 1 μm and 999 μm (e.g., between about 1 μm and 100 μm), wherein the second dimension is between about 1 μm and 999 μm (e.g., between about 1 μm and 100 μm), and wherein each hole is spaced apart from an adjacent hole by a distance (e.g., measured along the second surface), wherein a ratio between the distance and the first dimension is between about 2.1 and 2.4. In at least one embodiment, each protrusion has a ratio between the first dimension and the second dimension that is between about 1 and 1.3.

In at least one embodiment, the endoprosthesis is retrievable by, for example, a retrieval loop at a distal end of the stent.

Several methods of manufacturing an embodiment of the endoprosthesis are provided. One method of manufacturing includes forming a polymeric coating, wherein the polymeric coating includes a base and a tissue engagement portion. The base includes a first surface. The tissue engagement portion includes a second surface facing away from the first surface and includes a structure that defines a plurality of holes extending inwardly from the second surface toward the base. In one or more embodiments, the holes are arranged in a micropattern. The method further includes providing a stent having an inner surface defining a lumen and an outer surface; and attaching the base of the polymeric coating to the outer surface of the stent.

In one or more embodiments, the micropattern of holes may be made using lithography techniques, salt leaching, electrospinning, and/or laser ablation. In some embodiments that include a micropattern of micropillars, the polymeric coating can be formed using a mold having an inverse of the micropattern and injecting a polymeric material into the mold and, in some cases applying temperature or pressure to the mold, before the polymeric material cures; using soft lithography techniques, or by etching the polymeric coating from a layer of the polymeric material. In at least one embodiment, an adhesive layer is applied to at least one of a surface of the base and the outer surface of the stent. In at least one embodiment, the polymeric coating is formed as a tubular structure. In one or more embodiments, the polymeric coating is formed in a strip, which is wrapped (e.g., helically wrapped, circumferentially wrapped, randomly wrapped, etc.) about the outer surface of the stent.

BRIEF DESCRIPTION OF THE SEVERAL VIEWS OF THE DRAWING(S)

FIG. 2A shows a cross-section of the endoprosthesis shown in FIG. 1.

FIG. 3A shows a plan view of an endoprosthesis having a polymeric coating having a plurality of holes.

FIG. 3B shows a cross-section of the endoprosthesis shown in FIG. 3A.

FIG. 3C is an exemplary enlarged schematic of a polymeric coating having a plurality of holes representing the inset of FIG. 3B.

FIG. 3D is an exemplary enlarged schematic of a cross section of the polymeric coating of FIG. 3C having a plurality of holes representing the inset of FIG. 3B.

FIGS. 3E-3G are other exemplary enlarged schematics of a cross section of the polymeric coating of FIG. 3B (see inset) having a plurality of holes.

FIGS. 8A-8J show cross-sections of the micropillars of the polymeric coating shown in FIGS. 2B and 4-6.

FIGS. 9A-9J show plan views of embodiments of the polymeric coating shown in FIG. 2B.

FIG. 10A shows an embodiment of the polymeric coating of the present disclosure.

FIG. 12 is a view of a stent and polymeric coating during one or more methods of manufacturing an endoprosthesis.

DETAILED DESCRIPTION OF THE DISCLOSURE

Figure 1:
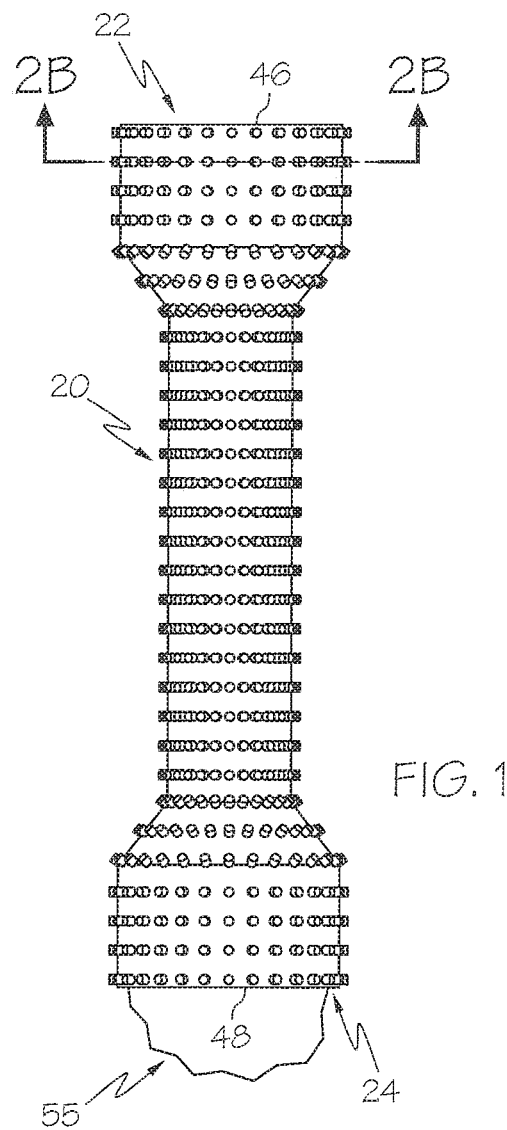
FIG. 1 shows a plan view of an endoprosthesis having a micropattern of microfeatures (e.g., micropillars).

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

The present disclosure relates to micropatterned polymeric coatings for use on medical devices. In some embodiments, the micropatterned polymeric coatings are utilized with implantable medical devices, such as stents, to reduce or prevent stent migration, particularly for stents used in the gastroesophageal system, including, but not limited to, esophageal, biliary, and colonic stents. In one or more embodiments, the micropatterned polymeric coating may include regularly or irregularly spaced, regularly or irregularly shaped micro-scale holes (e.g., voids, spaces, channels, passages, etc.) that may promote, for example, controlled cell migration and tissue ingrowth. Ingrowth of tissue into the micropatterned polymeric coatings (e.g., into the holes) may reduce stent migration by anchoring the stent to a body lumen wall (e.g., via controlled cell ingrowth, etc.). In one or more embodiments, the micropatterned polymeric coating may include and/or be formed from a biodegradable material, which may allow, for example, atraumatic stent removal in one or more applications. The stents described in this application may be used in the trachea, the cardiovascular system, and elsewhere in the body (e.g., any body lumen).

FIGS. 1 and 2A show an esophageal endoprosthesis 20 of the present disclosure with a proximal end 22 and a distal end 24. The endoprosthesis 20 includes an expandable stent 40 and a polymeric coating 50. Expandable stent 40 can be self-expanding, balloon expandable, or hybrid expandable. In one or more embodiments, expandable stent 40 is a braided stent that includes a plurality of wires and/or filaments that collectively form a braided construction. Embodiments of the expandable stent 40 contemplate stents having a constant diameter, one or more tapers, one or more flares and/or other changes in diameter in the body and/or at one or more ends. The expandable stent 40 has an inner surface 42, an outer surface 44, a first end 46 and a second end 48, and the polymeric coating 50 is disposed about at least a portion of the outer surface 44. In at least one embodiment, the polymeric coating 50 substantially covers the entire outer surface 44 of the expandable stent 40. In some embodiments, the polymeric coating 50 covers a portion of the outer surface 44 of the expandable stent 40 (e.g., at least 60%, at least 80%, at least 90%, at least 95%, at least 99% of the area of the outer surface 44). As shown in FIG. 2A, the polymeric coating 50 can be directly connected to the outer surface 44 of the expandable stent 40. In one or more embodiments, the polymeric coating 50 can be connected to the outer surface 44 of the expandable stent 40 using an adhesive or other means of attaching the coating to the device. In at least one embodiment, the polymeric coating at least partially covers the inner surface 42 also. In at least one embodiment, partial coverage can include partial coverage of the perimeter and/or the length. In one or more embodiments, the polymeric coating 50 may be disposed along the entire stent length, may be incorporated into a silicone coating (e.g., in a patchwork), may be applied to another coating, may be disposed on one or more stent flares, and/or helically wrapped around a body of the stent.

Figure 2B:
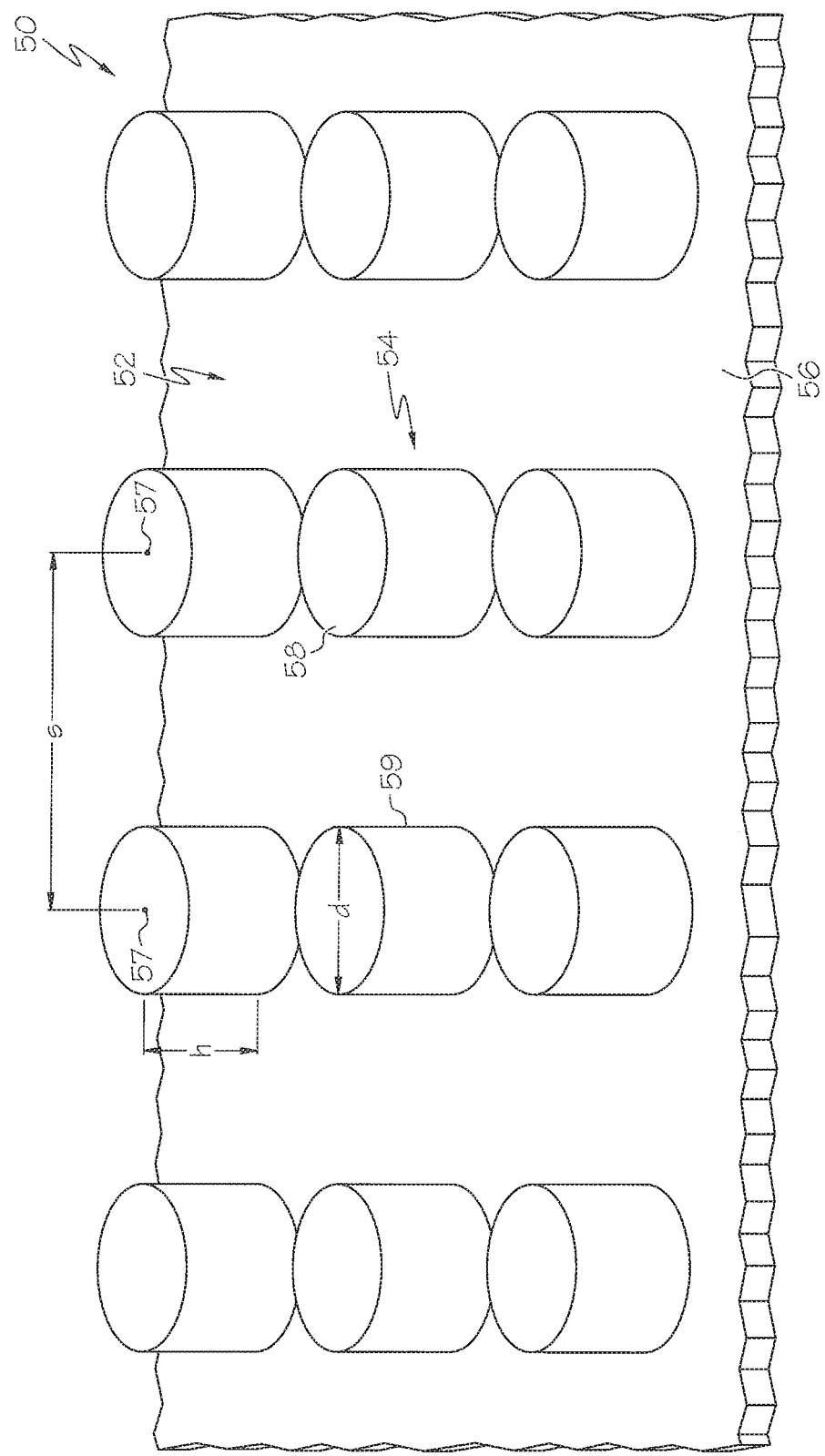
FIG. 2B is an exemplary enlarged view of the polymeric coating of the endoprosthesis shown in FIG. 1.
Figure 4:
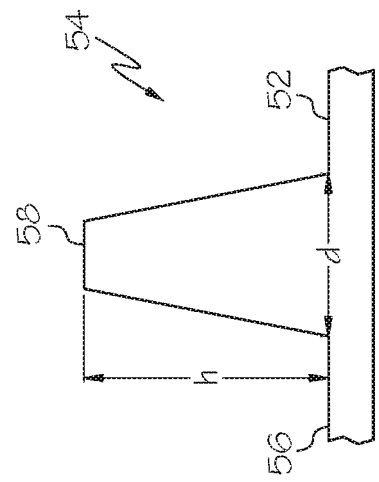
FIG. 4 shows a cross-section of a portion of the polymeric coating shown in FIG. 2B.

In at least one embodiment, shown in FIGS. 2A and 2B, the polymeric coating 50 includes a base 52 and a plurality of protrusions, such as micropillars 54, extending outwardly from the base 52. In at least one embodiment, the micropillars are incorporated (e.g., seamlessly incorporated, etc.) into the base of the coating. In at least one embodiment, the base 52 is coterminous with the expandable stent 40. What is meant by "coterminous" is that the base 52 of the polymeric coating 50 and the expandable stent 40 have the same boundaries, cover the same area, and are the same in extent. In other words, the expandable stent 40 and the base 52 each have first and second ends, and the expandable stent 40 and the base 52 extend between their first and second ends. The first end of the expandable stent 40 is the same as first end of the base 52, and the second end of the expandable stent 40 is the same as the second end of the base 52. Since the expandable stent 40 and the base 52 extend between their first and second ends, the expandable stent 40 and the base 52 have the same boundaries, cover the same area, and are the same in extent. Thus, the base 52 and the expandable stent 40 are coterminous. The expandable stent 40 and the base 52 therefore are coterminous in at least one embodiment. Also, base 52 is tubular in at least one embodiment.

In at least one embodiment, shown in FIGS. 3A-3G, the polymeric coating 50 may include a base 52 and tissue engagement portion 53. Base 52 includes a first surface 71 attached (e.g., adhered, bonded, etc.) to the outer surface of the stent 40 (not shown) in FIGS. 3C-3D. Tissue engagement portion 53 includes a second surface 72 facing outwardly from the stent 40. The second surface may define a plurality of openings from which holes 54*h* may extend. The tissue engagement portion 53 may include structure 61 defining a plurality of holes 54*h*, such as the cylindrical microholes 54*h* (FIGS. 3C-3D), extending inwardly from the second surface 72 of the tissue engagement portion 53 toward base 52. In at least one embodiment, the structure 61 is seamlessly incorporated into the base 52 of the coating 50. In at least one embodiment, the base 52 is coterminous with the expandable stent 40. As shown in FIG. 3C, the holes 54*h* are arranged in a micropattern, which may include regularly shaped holes (e.g., FIGS. 3C, 3E, and 3F) and/or irregularly shaped holes (FIG. 3G), and which may include holes 54*h* arranged in a regular pattern (e.g., FIGS. 3C, 3F) and/or in an irregular micropattern (e.g., FIGS. 3E, 3G). In one or more embodiments, the base 52 covers the apertures of the stent 40 (e.g., FIG. 3A).

In one or more embodiments, the plurality of openings in the second surface 72 includes a first opening and a second opening and the plurality of holes includes at least a first hole extending from the first opening and a second hole extending from the second opening, wherein the first hole and second hole are in fluid communication via a channel disposed between the first surface and the second surface. For example, in FIG. 3E, there is a plurality of holes 54*h* that are shown to be located at the second surface 72 and between the second surface and the base 52. In FIG. 3E, each of the holes 54*h* below the second surface 72 is meant to be in fluid communication with at least one hole 54*h* at the second surface 72 which would allow tissue ingrowth (e.g., cell migration) from the second surface toward the base 52. FIG. 3F shows a regular arrangement of a plurality of holes 54*h* at and below the second surface 72. Similarly, the holes 54*h* between the second surface 72 and the base 52 are meant to be in fluid communication with at least one hole 54*h* at the second surface, such that tissue ingrowth is possible into the holes 54*h*. In some embodiments, a network of holes may be formed wherein cells may invade. A network of holes may be useful in that the coating may allow for tissue ingrowth while maintaining the stent's relatively low profile (relative to a stent having additional scaffolding on the outside of the stent for tissue ingrowth and reducing stent migration) while reducing or preventing reocclusion of the lumen. Additionally, structure 61 may be adapted to allow controlled cell ingrowth at an implantation site and allow atraumatic removal of the stent (e.g., before, during, and/or after cell ingrowth occurs).

In one or more embodiments, one or more holes 54*h* may extend completely through the thickness of the coating 50. In one or more embodiments, one or more of the holes 54*h* is a blind hole (e.g., a cavity, an indentation, a hole having a bottom, a hole that does not extend from the second surface 72 to the first surface 71. For example, FIGS. 3C-3D depict a plurality of holes 54*h* that are blind holes. In one or more embodiments, all of the holes 54*h* are blind holes (i.e., no holes extend from the second surface to the first surface).

As shown in FIG. 3G, structure 61 of the tissue engagement portion 53 may include a plurality of intertwining fibers, wherein the arrangement of fibers creates a network of holes 54*h* between the second surface 72 and the base 52. In the present disclosure, the size of a hole 54*h* may be defined by a diameter of the largest sphere that could fit within a particular three-dimensional space between the second surface 72 and the base 52.

As may be implied from FIGS. 3A-3G, the first surface 71 may define a length and a width of the coating 50 and the second surface 72 of the coating 50 may extend around the plurality of holes continuously along at least one of the length and width of the coating. For example, second surface 72, as depicted in FIG. 3C extends continuously around a plurality of holes 54*h* along the coating length and width.

Figure 5:
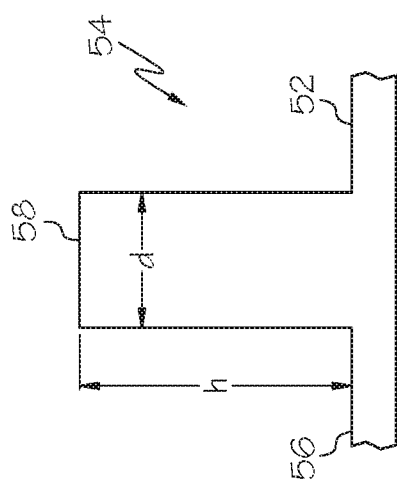
FIGS. 5-7 show cross-sections of portions of embodiments of the polymeric coating.
Figure 7:
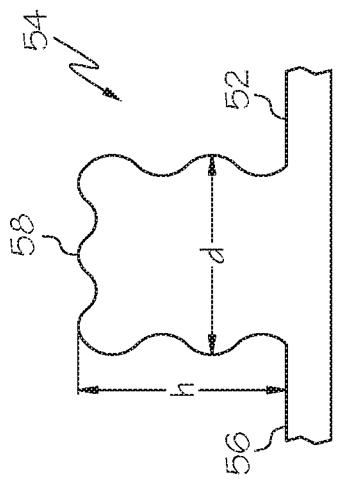
Figure 6:
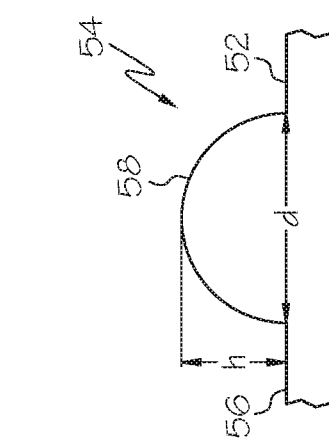

In some embodiments as shown in FIGS. 2B and 4-7, the micropillars are cylinders (FIG. 2B), prisms with a rectangular or polygonal base (FIG. 4), pyramids (FIG. 5), bumps (FIG. 6), or has a non-traditional shape with a plurality of bumps and ridges on multiple surfaces that do not define a cross-section that is circular, square, polygonal, etc. (FIG. 7). Each micropillar can have a circular cross-section (FIG. 8A), square cross-section (FIG. 8B), rectangular cross-section (FIG. 8C), star-shaped cross-section (FIG. 8D), hexagonal cross-section (FIG. 8E), pentagonal cross-section (FIG. 8F), heptagonal (FIG. 8G), octagonal cross-section (FIG. 8H), nonagonal cross-section (FIG. 8I), decagonal cross-section (FIG. 8J), other polygonal cross-sections, or non-traditional shaped cross-sections. Each cross-section has a first dimension h that is the greatest distance between the outer surface of the base and the end of the pillar and a second dimension d that is the greatest distance between two opposite sides (e.g., of the pillar). For example, for the circular cross-section the second dimension d is the diameter, for the square d is between two sides, for the rectangle, the major dimension is between the two shorter sides, for the star, the major dimension is between two points, for the hexagon the major dimension is between two opposite points. In some embodiments, the second dimension d is between midpoints of two opposite sides. In at least one embodiment, a cross section of the micropillar taken in the radial direction has at least four sides. Embodiments of the present disclosure contemplate polygonal cross-sections having all sides of equal length, combinations of sides of equal length and unequal length, or all sides of unequal length. Embodiments of the present disclosure contemplate multiple pillars of multiple cross-sectional shapes including traditional shapes (e.g. circles, squares, rectangles, hexagons, polygons, etc.) and non-traditional shapes having a perimeter where at least a portion of the perimeter is curvilinear. In at least one embodiment, the micropillars are solid structures, but in other embodiments they can be hollow structures. In at least one embodiment, each micropillar has a constant cross-section, but in other embodiments the micropillars have variable cross-sections. In at least one embodiment, a micropillar extends perpendicularly from a base (e.g., FIG. 4). In at least one embodiment, a micropillar extends from a base in a non-perpendicular angle (e.g., FIG. 5) wherein geometric center 57 (see, e.g., FIG. 2B) of the end 58 of the micropillar is offset laterally from the geometric center of the area of the base covered by the micropillar (e.g., FIG. 5). In FIG. 5, a longitudinal axis of the micropillar 54 extending through the geometric centers of the lateral cross-sections forms an angle that is less than 90 degrees with base 52. In at least one embodiment, the plurality of micropillars 54 can be arranged in one or more particular micropatterns.

In one or more embodiments, holes 54*h* (see FIG. 3C) may take any of the shapes and dimensions (e.g., h, d, s of FIG. 2B) described herein regarding micropillars 54. For example, holes 54*h* may take the shape of a prism having a cross-section defined by any of the shapes of FIGS. 8A-8J. In one or more embodiments the shape of holes 54*h* may be selected from a cylinder, a rectangular prism, a prism with a polygonal base, a sphere, a spheroid, and an ellipsoid. In other examples, structure 61 may define holes 54*h* having the same shapes as those shown for micropillars 54 in FIGS. 4-7. Of course, the height h of the holes 54*h* may be any height up to and not greater than the thickness of the polymeric coating 50 (e.g., the sum of thickness of the base 52 and the tissue engagement portion 53). In one or more embodiments, the base is continuous and is devoid of holes extending therethrough. In one or more embodiments, the base 52 includes a base structure that defines a plurality of base holes (e.g., which may be in fluid communication with the plurality of holes 54*h* of the tissue engagement portion 53).

Although not wishing to be bound by theory, the micropattern may affect the strength of the frictional engagement or interlock between the endoprosthesis and the vessel wall. Likewise, the micropattern is dependent upon the desired frictional engagement or interlock between the microfeatures (e.g., micropillars, holes, etc.) of the endoprosthesis and the tissue. For this reason, in at least one embodiment, a particular microstructure can be selected that has a micropattern geometry and dimensions suitable for a particular application (e.g., implantation site, biological tissue, desired tissue engagement properties, etc.).

Throm Quinlan et al. disclose that "[c]ells such as fibroblasts, endothelial cells, and muscle cells actively sense both the external loading applied to them (outside-in signaling) and the stiffness of their surroundings (inside-out signaling). They respond to these stimuli with changes in adhesion, proliferation, locomotion, morphology, and synthetic profile." See Throm Quinlan et al., "Combining Dynamic Stretch and Tunable Stiffness to Probe Cell Mechanobiology In Vitro," 2011, PLoS ONE 6(8): e23272. Thus, specific structure of micro-scale features (e.g., holes, voids, pores, etc.) as well as coating material properties may be useful in controlling cell behavior.

It should be noted that the surface features of micropillars or holes described herein (e.g., bumps of FIG. 6, bumps and ridges of FIG. 7, etc.) may have one or more micro-scale or nano-scale (e.g., from about 1 nanometer to about 999 nanometers) dimensions.

In at least one embodiment, the micropillars in the micropattern all have the same shape, and in other embodiments, the micropillars vary in shape along the polymeric coating. Thus, in at least one embodiment, the micropattern can include portions where the micropillars have a first configuration and portions where the micropillars have a second configuration. Moreover, embodiments include the polymeric coating having only one micropattern or the polymeric coating having multiple micropatterns. Thus, the polymeric coating can be tailored to specific structural characteristics of the body lumen (e.g., a vessel, etc.) and a desired frictional engagement or interlock can be achieved, while using a single stent.

Similarly, in one or more embodiments, holes may be configured and arranged in the same manner described herein for micropillars. That is, in at least one embodiment, the holes 54*h* in the micropattern may all have the same shape, and in other embodiments, the holes may vary in shape along the polymeric coating. Thus, in at least one embodiment, the micropattern can include portions where the holes have a first configuration and portions where the holes have a second configuration. Moreover, embodiments include the polymeric coating having only one micropattern (e.g., of holes, of micropillars, etc.) or the polymeric coating having multiple micropatterns (e.g., two or more different micropatterns of holes, two or more micropatterns of micropillars, one or more micropattern of holes in combination with one or more micropatterns of micropillars). Thus, the polymeric coating can be tailored to specific structural and/or anatomical characteristics of the body lumen (e.g., a vessel, etc.) and a desired frictional engagement or interlock can be achieved, while using a single stent. In one or more embodiments, a micropattern may include one or more holes in combination with one or more micropillars (e.g., a micropattern including a first number of holes alternating with a second number of micropillars, etc.). In one or more embodiments, a polymeric coating may include a micropattern of micropillars and a micropattern of holes, wherein the micropatterns may or may not overlap.

In at least one embodiment, the dimension d (e.g., of holes, of micropillars, etc.) is between 1 μm and 100 μm. In at least one embodiment, the dimension d is between about 14 μm and 18 μm. In at least one embodiment, the dimension d is at least equal to the dimension h (e.g., of holes, of micropillars, etc.). In at least one embodiment, a ratio of h to d is between about 1 and 1.3. In at least one embodiment, two adjacent micropillars are spaced apart by a distance s (shown in FIG. 2B). In at least one embodiment, the ratio of the spacing s to the dimension d is between about 2.1 and 2.4.

In some embodiments, the ends 58 of the protrusions, such as micropillars 54, that are furthest away from the outer surface of the base can be shaped to improve tissue attachment. In one or more embodiments, the ends can be tapered, pointed, rounded, concave, convex, jagged, or frayed. The ends 58 of each protrusion (micropillar 54) can include a plurality of pillars on an even smaller scale than micropillars 54.

Similarly, in some embodiments, the second surface 72 of the tissue engagement portion can be adapted (e.g., shaped, textured, modified, etc.) to improve tissue attachment. In one or more embodiments, the lateral and/or bottom surfaces of the holes 54*h* can be tapered, pointed, rounded, concave, convex, jagged, or frayed. The end 58 of each hole 54*h* may include a plurality of pillars and/or holes on an even smaller scale than holes 54*h*.

In at least one embodiment, the protrusions such as micropillars 54 can also include features such as smooth surfaces, rough surfaces 55*a* (FIG. 9A), a plurality of bumps 55*b* extending outwardly from a surface of the micropillar (FIG. 9B), a plurality of indentations 55*c* extending inwardly from a surface of the micropillar (FIG. 9C), a plurality of ridges 55*d* on a surface of the micropillar (FIG. 9D), a tip 55*e* at or near the end of the protrusion that either softer or more rigid than the remainder of the protrusion (FIG. 9E), a frayed tip 55*f* (FIG. 9F), a convex (e.g., rounded) tip (FIG. 9G), a flared (e.g., flat top) tip (FIG. 9H), a concave (e.g., rounded) tip (FIG. 9I), a tip having a first dimension dt that is greater than a dimension d of the micropillar column extending between the base 52 and the tip (FIG. 9J), and other features that may impart useful (e.g., desirable) gripping, stiffness, or flexibility characteristics for the endoprosthesis, and any combination of features thereof. In at least one embodiment, the tip 55*e* can include a different material than the remainder of the protrusion. Similarly, the end 58 and lateral surfaces 59*h* of holes 54*h* may be shaped to improve tissue attachment similar to that described above with respect to micropillars 54. For example, holes 54*h* may include features such as smooth surfaces, rough surfaces, a plurality of bumps extending outwardly from a surface of the hole 54h, a plurality of indentations extending inwardly from a surface of the hole 54h, a plurality of ridges on a surface of the hole 54h, a frayed end 58, a convex (e.g., rounded) end, a flared (e.g., flat bottom) end, a concave (e.g., rounded) end, a bottom having a first dimension dt that is greater than a dimension d of a cylindrical column extending between the second surface 72 and the end, and other features that may impart useful (e.g., desirable) gripping, stiffness, or flexibility characteristics for the endoprosthesis, and any combination of features thereof.

FIG. 2B shows an enlarged view of the polymeric coating 50 having micropillars. In at least one embodiment, the micropillars are cylinders that each have a diameter d and a height, h measured from an outer surface 56 of the base 52 to an end 58 (e.g., top surface, etc.) of the cylinder for micropillars. In at least one embodiment, the diameter d is between 1 μm and 150 μm (e.g., between 1 μm and 100 μm, between 1 μm and 50 μm, between 1 μm and 20 μm, etc.). In at least one embodiment, the diameter d is between about 14 μm and 18 μm. In at least one embodiment, the diameter d of the micropillar is at least equal to its height h. In at least one embodiment, a ratio of height h of the micropillar 54 to the diameter d of the micropillar 54 is between about 1 and 1.3. In at least one embodiment, the micropillars 54 each have a lateral surface 59. In at least one embodiment, two adjacent micropillars are spaced apart. The micropillars should be spaced apart enough to encourage engagement and/or interlocking, for example, via an engagement mechanism (e.g., tissue ingrowth, chemical bond, proximity attraction via van der Waals forces, etc.). For tissue ingrowth, for example, the micropillars should be spaced apart enough so that the tissue of the bodily vessel can fill the negative space (e.g., void space) between the pillars. If the spacing is too small, tissue ingrowth may not occur (e.g., the tissue may not be able to actually interlock). In at least one embodiment, the spacing between the micropillars is dependent upon (e.g., may be selected based upon) the particular type of tissue of the bodily vessel. In at least one embodiment, the spacing s measured between the centers 57 of one micropillar and an adjacent micropillar is greater than the diameter d of the one micropillar. In at least one embodiment, the ratio of the spacing s to the diameter d is between about 2.1 and 2.4.

FIG. 3C shows an enlarged view of the polymeric coating 50. In at least one embodiment, the holes 54h are cylinders that each have a diameter d and a height, h measured from the second surface 72 of the tissue engagement portion to an end 58 (e.g., bottom surface, etc.) of the cylinder. In at least one embodiment, the diameter d is between 1 μm and 150 μm (e.g., between 1 μm and 100 μm, between 1 μm and 50 μm, between 1 μm and 20 μm, etc.). In at least one embodiment, the diameter d is between about 14 μm and 18 μm. In at least one embodiment, the diameter d of the hole is at least equal to its height h. In at least one embodiment, a ratio of height h of the hole 54h to diameter d of the hole is between about 1 and 1.3. In at least one embodiment, the holes 54h each have a lateral surface 59h. In at least one embodiment, two adjacent holes 54h are spaced apart (e.g., spaced apart at the second surface 72 of the tissue engagement portion 53). The micropillars should be spaced apart enough to encourage engagement and/or interlocking, for example, via an engagement mechanism (e.g., tissue ingrowth, chemical bond, proximity attraction via van der Waals forces, etc.). For tissue ingrowth, for example, the holes should be spaced apart enough so that the tissue of the bodily vessel can fill the negative space (e.g., void space) within the holes. If the spacing between holes is too large, tissue ingrowth may not be able to occur (e.g., the tissue may not be able to actually interlock). In at least one embodiment, the spacing between the holes may be is dependent upon (e.g., may be selected based upon) the particular type of tissue of the bodily vessel. In at least one embodiment, the spacing s measured between the centers 57 of one hole and an adjacent hole along the second surface 72 is greater than the diameter d of the one hole (e.g., greater than the sum of the radii of the one hole and the adjacent hole). In at least one embodiment, the ratio of the spacing s between adjacent holes to the diameter d of the holes is between about 1.01 and 2.0 (e.g., between about 1.01 and 1.5).

Figure 10B:
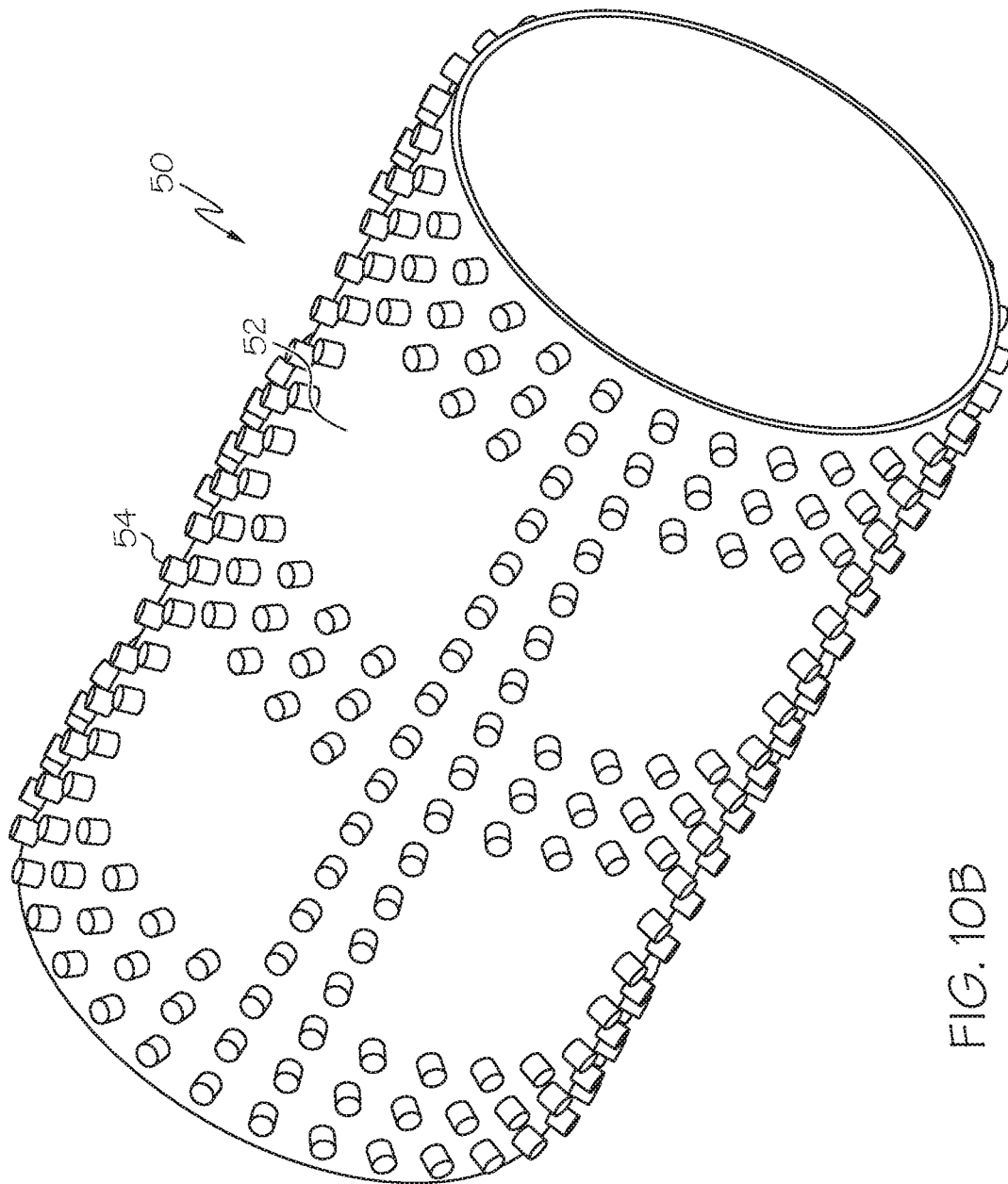
FIG. 10B shows an embodiment of the polymeric coating of the present disclosure.
Figure 10E:
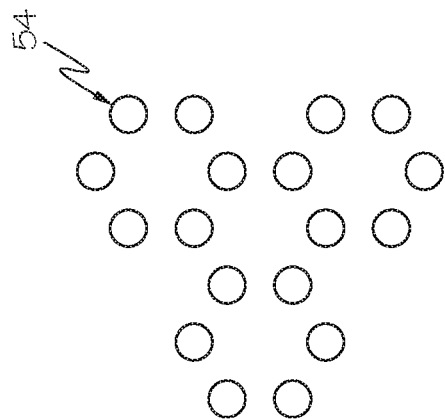
FIGS. 10C-10E show embodiments of arrays of microfeatures (e.g., micropillars) forming a micropattern.
Figure 10D:
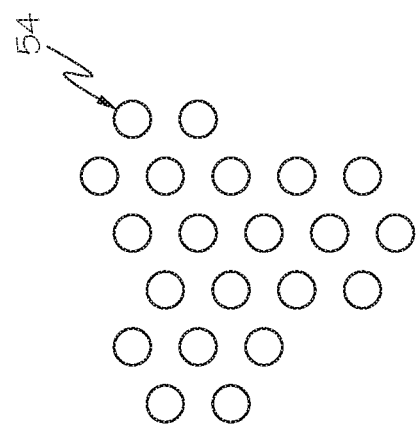
Figure 10C:
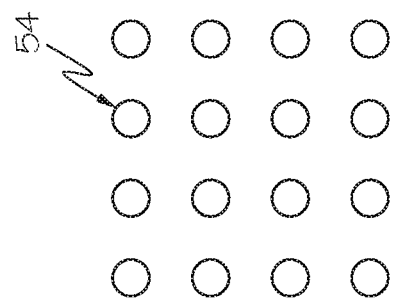

In at least one embodiment, the micropillars and/or holes are spaced apart equidistantly in the micropattern. In at least one embodiment, the micropattern of micropillars is a rectangular array (e.g., FIG. 2B, FIG. 3C, FIG. 10C). In at least one embodiment, the micropattern is a grid pattern (e.g., a square array as in FIGS. 2B, 3C, 10C, 11). In at least one embodiment, the micropattern is a regular n-polygonal array (e.g., hexagonal array in FIGS. 10D, 10E), wherein a micropillar or hole may be present in the center of the polygon (e.g., FIG. 10C, FIG. 10D, etc.) or may not be present in the center of the polygon (e.g., FIG. 10E). In other words, in the micropattern, the micropillars and/or holes are arranged in rows and columns in the micropattern, wherein the rows and columns may or may not be perpendicular. For example, the micropattern of FIG. 10C includes rows and columns that are perpendicular, whereas the micropattern of FIGS. 10D and 10E includes rows and columns that are not perpendicular. In one or more embodiments, each micropillar or hole has a longitudinal axis and the micropillars are axially aligned in at least one of the axial direction (e.g., arranged in a row parallel to a longitudinal axis of a stent) and the circumferential direction of the endoprosthesis (e.g., arranged in a row extending circumferentially around a longitudinal axis of a stent). In at least one embodiment, the micropattern of micropillars or holes includes any or all of the features described in this paragraph. In some embodiments, like the embodiments shown in 10A and 10B, the micropattern may cover only a portion of the base 52 rather than the entire base 52. The micropattern of micropillars or holes may be helically disposed on the base 52, as shown in FIG. 10A. In one or more embodiments, as shown in FIG. 10B, a first micropattern may be disposed longitudinally along the base 52 and a second micropattern is disposed circumferentially about the base so that the micropattern forms a "window pane"-like configuration. As depicted in FIG. 10B, the micropillars arranged in a row (e.g., parallel to a longitudinal axis of a stent) may be continuous rows or discontinuous rows (e.g., aligned row segments separated by a gap having a dimension greater than s), wherein the length of the discontinuity may have any length (e.g., 2 or more times the dimension s). For example, the embodiment depicted in FIG. 10B shows discontinuous rows (and circumferentially oriented columns) extending across the window panes wherein the length of the discontinuity is five times the dimension s (see FIG. 2B) whereas the embodiment depicted in FIG. 10E shows discontinuous rows (and nonperpendicularly oriented columns) wherein the length of the discontinuity is two times the dimension s (see FIG. 2B). In terms of the dimension s shown in FIGS. 2B and 3C, a row and/or column discontinuity may have any length (e.g., at least 2 times s, at least 5 times s, at least 10 times s, at least 50 times s, at least 100 times s, at least 500 times s, at least 1000 times s, etc.). Similarly, any of the micropatterns described herein may include one or more holes instead of one or more micropillars (e.g., all holes).

Regarding the material used for the polymeric coating 50, it is useful that the material be flexible and/or elastic enough to create an effective interlock with the tissue, be able to withstand the processing for creating the polymeric coating 50, to accommodate stent mechanics such as elongation and conformability to tortuous anatomy. Examples of acceptable materials include, but are not limited to, flexible silicones, hydrogels, mucoadhesive substrate, pressure-sensitive adhesives, and other suitable elastomers, such as synthetic rubbers. In one or more embodiments, a coating having a micropattern may include and/or be formed from a biologically-derived protein structure (e.g., collagen, etc.). Other acceptable materials include any flexible, biocompatible, and non-biodegradable polymer. For palliative treatment stent applications, it may be useful for the coating to include one or more non-biodegradable polymers and/or a material having a degradation profile that may be useful for the particular stent application and implantation site. In one or more embodiments, the coating may be biodegradable in order to, for example, allow stent removal (e.g., after some portion or all of the coating has degraded). Applications in which it may be useful to remove a stent include support during perforation healing, dilatation of benign structures, and bridge to surgery.

In at least one embodiment, the polymeric coating 50 (e.g., having micropillars 54 and/or holes 54*h*) may include proteins capable of engaging and/or interlocking with the tissue wall in a biochemical manner. In one or more embodiments, the polymeric coating 50 may include (e.g., be laced with) one or more growth factors that promote cell migration and/or control the amount and timing of cell invasion/tissue ingrowth between micropillars and/or within holes. In at least one embodiment, the polymeric coating 50 may include at least one therapeutic agent. In other embodiments, an additional coating may be applied to the polymeric coating 50 that includes a therapeutic agent. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, etc. Where an agent includes a genetic therapeutic agent, such a genetic agent may include but is not limited to: DNA, RNA and their respective derivatives and/or components. Where a therapeutic agent includes cellular material, the cellular material may include but is not limited to: cells of human origin and/or non-human origin as well as their respective components and/or derivatives thereof. In one or more embodiments, a suitable therapeutic agent (e.g., small organic molecules, peptides, oligopeptides, proteins (e.g., "hedgehog" proteins, etc.), nucleic acids, oligonucleotides, genetic therapeutic agents, non-genetic therapeutic agents, vectors for delivery of genetic therapeutic agents, cells, therapeutic agents identified as candidates for vascular treatment regimens, etc.) may include any one or more of those disclosed in U.S. Pat. No. 8,267,992 (Atanasoska et al.), which is incorporated by reference herein in its entirety. In one or more embodiments, one or more therapeutic agents may be included within or on polymeric coating 50, including the micropillars 54 and/or holes 54*h*.

In one or more embodiments, the base 52 may be formed from the same material as the micropillars 54 and/or the structure 61 of the tissue engagement portion 53. In one or more embodiments, the micropillars 54 and/or structure 61 are formed from one material and the base 52 is formed from a different material. In one or more embodiments, the micropillars 54 and/or structure 61 are formed with layers of material, and these layers can be the same material or can be different materials depending on the characteristics required for the desired frictional engagement of the endoprosthesis with the vessel wall.

Because the endoprosthesis 20 has improved frictional engagement with the tissue wall when inserted into a lumen of the patient, removal of the stent may be more difficult with some traditional removal techniques. In at least one embodiment, shown in FIG. 1, the endoprosthesis 20 is provided with a suture or removal loop 55 on one end of the stent. In at least one embodiment, the removal loop 55 is provided on a distal end of the stent. It should be noted that references herein to the term "distal" are to a direction away from an operator of the devices of the present disclosure, while references to the term "proximal" are to a direction toward the operator of the devices of the present disclosure. While sutures or removal loops are well known in the art for removing endoprosthesis, sutures or removal loops have been provided on the proximal end of the stent, in other words the closest end to the practitioner. Here, the suture or removal loop is applied to the opposite end of the endoprosthesis. In at least one embodiment, the practitioner grabs the loop from inside the endoprosthesis, and by applying an axial force to the loop, the distal end of the endoprosthesis is pulled through the lumen of the endoprosthesis itself. Thus, the micropillars are peeled away from the vessel wall while the stent is flipped inside out to remove the endoprosthesis. In other embodiments, the practitioner may grab the loop from outside the endoprosthesis or at an end of the endoprosthesis. Although not shown in FIG. 3A, a suture or removal loop 55 may be provided on one end of the stent of FIG. 3A.

To manufacture the endoprosthesis 20, several methods can be employed. The polymeric coating 50 can be formed (e.g., molded) separately from the stent (e.g., as a polymeric film, a hydrogel film, a thin fibrous network, etc.) and then adhered to the stent (e.g., an outer surface of the stent) with an optional adhesive layer 60 disposed between the outer surface of the stent and the base (e.g., the first surface) of the polymeric coating (e.g., applied to at least a portion of one or both of the first surface of the base and the outer surface of the stent). Polymeric material can be injected into a mold with the inverse of the micropattern to create the polymeric coating having a micropattern of microfeatures (e.g., micropillars, holes, etc.). Also, the polymeric material can be pulled through a mold using a vacuum pump system. In at least one embodiment, the polymeric coating can be created using soft lithography techniques. In one or more embodiments, etching techniques can be used to create the coating, wherein material is taken away from a layer of the coating material to create the micropattern of the polymeric coating 50. In yet another embodiment, a technique called hot embossing can be used, which involves stamping partially cured polymer into the desired shape of the polymeric coating and then curing it before it is applied to the stent. Stamping may or may not include the use of a solvent. In one or more embodiments, a stent may be coated by any suitable method (e.g., spraying, dipping, injection molded, etc.), followed by the introduction of holes into the coating after the stent coating. In some embodiments, a fibrous network with micro-scale holes (e.g., voids) may be formed by electrospinning one or more fibers on a pre-coated stent. In one or more embodiments, a laser ablation process may be used (e.g., using one or more appropriately sized laser beams (e.g., same or different sizes depending on the desired pattern) to remove material from a coating in order to form one or more micropillars and/or one or more microholes.

In one or more embodiments, one or more portions of coating may be deployed into a body lumen separately from a stent (e.g., as one or more pads, etc.). Then, for example, a pressure-sensitive adhesive may be applied to an applicable portion of a stent meant to attach to the pre-deployed coating (e.g., biointeractive pads). The radial expansive force of the stent during and after deployment may activate the adhesive and adhere the stent to the coating previously deployed in a body lumen.

In one or more embodiments, a polymeric coating 50 having holes (e.g., microholes) may be formed by using a technique called particulate leaching (e.g., salt leaching), wherein a composite material is formed from one or more polymeric materials and one or more particulates (e.g., salts), followed by leaching the one or more particulates (e.g., salts) from the composite material (e.g., with a solvent) resulting in a composite and/or polymeric material having holes or voids where the one or more particulates (e.g., salts) were removed.

In one or more embodiments, a polymeric coating having a plurality of holes may be formed by a technique called electrospinning (e.g., using an electrical charge to draw very fine fibers from a liquid), wherein the polymeric coating includes a plurality of fibers arranged at or near the base forming holes (e.g., a network of holes, a network of voids) between the fibers.

In one or more embodiments, the use of salt leaching and/or electrospinning provides a polymeric coating 50 having one or more holes 54*h* that form a network of holes (e.g., a plurality of holes in fluid communication below the base). In some embodiments, cell ingrowth may be enhanced when the polymeric coating includes a network of holes. In one or more embodiments, any of a wide variety of therapeutic agents (e.g., growth factors) including, but not limited to, those described herein may be included on, within, and/or in combination with a network of holes to promote tissue ingrowth when the micropatterned polymeric coating contacts tissue.

Figure 11:
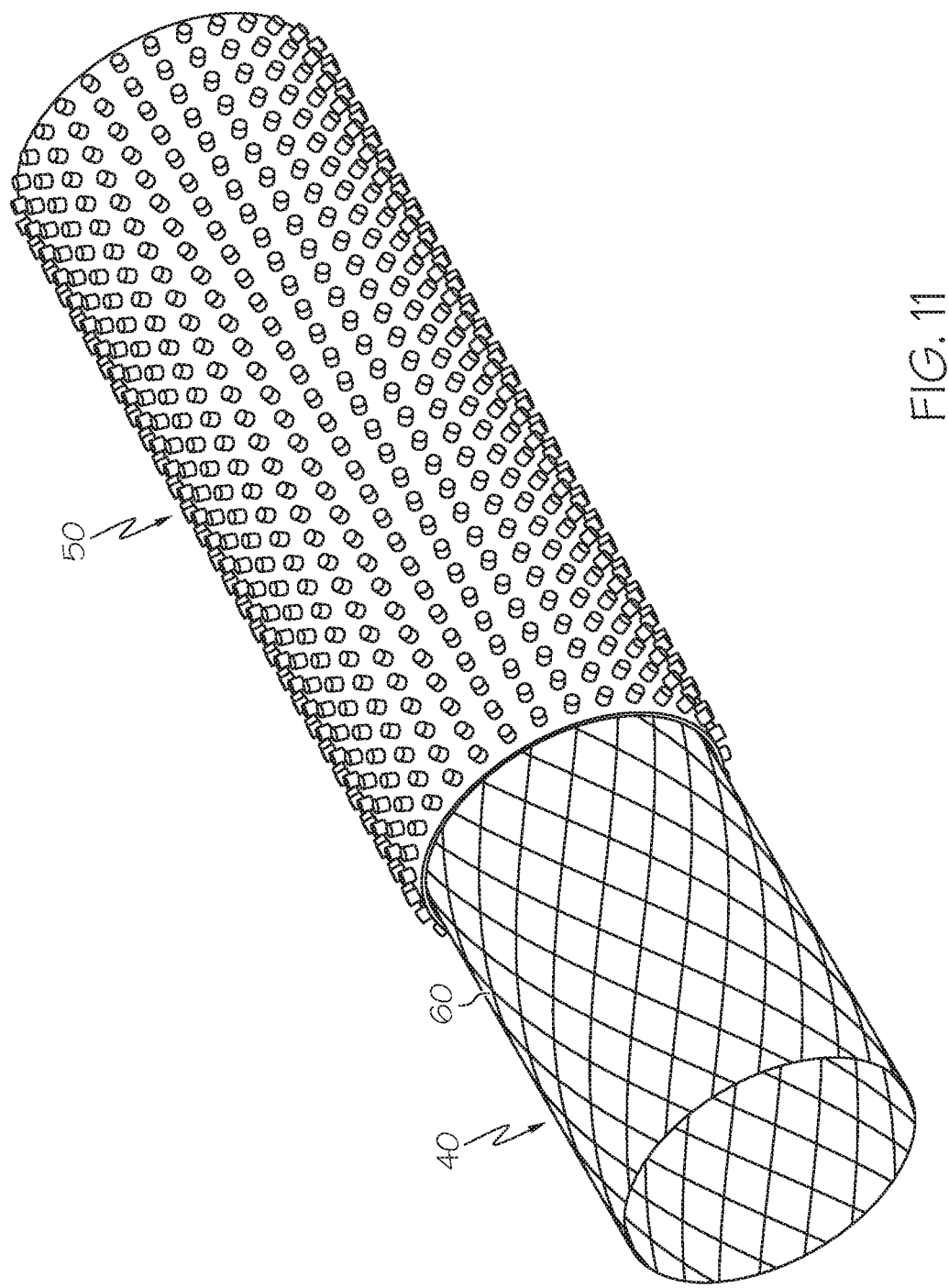
FIG. 11 is a view of a stent and polymeric coating during one or more methods of manufacturing an endoprosthesis.

In at least one embodiment, as shown in FIG. 11, the coating 50 can be molded as a substantially tubular structure with a lumen defined by the base of the coating. An adhesive layer 60 can be applied to either the stent or to at least a portion of the inner surface of the base of the coating. In at least one embodiment, the adhesive layer 60 may substantially cover the entire inner surface of the base of the coating. The stent 40 can be inserted into the lumen of the coating 50. In at least one embodiment, heat and/or pressure may be applied to ensure proper adhesion of the coating 50 to the stent 40 via the adhesive layer 60. The adhesive layer may include silicone coatings, other suitable adhesives, or priming solutions that enable the coating to adhere to the metal stent (or stent coating thereon). In one or more embodiments, as shown in FIG. 12, rather than being molded as a tubular structure, the coating 50 can be molded as a strip attached to the outer surface 44 of the stent 40. In some embodiments, the strip can be applied as perimeter strips attached circumferentially about at least a portion of the circumferential perimeter of the stent. In some embodiments, the strip can be a longitudinal strip attached to the stent in a longitudinal direction. In some embodiments, the stent can be helically wrapped about the stent, as shown in FIG. 12. In some embodiments the coating may be applied as a single strip or as multiple strips. Where the coating is applied as multiple strips, directly adjacent strips may abut one another or may be spaced apart from one another. In at least one embodiment, the strips may be partial tubular structures that extend along the length of the stent but only cover a portion of the circumference of the stent. In some embodiments, a portion of stent 40 may be exposed. An adhesive layer 60 can be applied to either the stent or to at least a portion of the base of the coating. In at least one embodiment, heat and/or pressure may be applied to ensure proper adhesion of the coating 50 to the stent 40 via the adhesive layer 60. In at least one embodiment, discrete micropatterns of micropillars can be formed on and/or attached directly to either the stent 40 or the polymeric coating 50.

In one or more embodiments, the polymeric coating 50 can be formed by dip-coating the stent 40 in the coating material without needing an additional adhesive layer to connect the coating 50 to the stent 40. For example, the stent 40 can be inserted into a mold, which includes a cavity and a tubular member. The cavity is defined by an inner wall of mold, which is an inverse of the desired micropattern. The stent 40 rests on the tubular member such that the inner surface of the stent is disposed about the tubular member. The mold with the stent 40 can be dipped into the coating material so that the coating material fills the mold and attaches to the stent 40. In some embodiments, temperature changes and/or pressure changes may be applied to the mold to cure the coating material. Once the coating material cures to form the polymeric coating 50, the endoprosthesis 20 can be removed from the mold. Alternatively, the polymeric coating 50 can be injection molded onto the stent using a similar mold. The coating material is injected into the mold rather than the mold being dipped into the coating material.

A description of some exemplary embodiments of the present disclosure is contained in the following numbered statements:

Statement 1. An endoprosthesis having an expanded state and an unexpanded state, the endoprosthesis comprising:

a stent, wherein the stent has an inner surface defining a lumen, an outer surface, a first end, a second end, and a stent thickness defined between the inner surface and the outer surface, wherein the stent defines a plurality of apertures extending through the stent thickness, wherein the apertures are arranged in a macropattern; and a polymeric coating attached to the outer surface of the stent, the polymeric coating comprising a base comprising a first surface attached to the outer surface of the stent; and a tissue engagement portion comprising a second surface facing outwardly from the stent, the tissue engagement portion comprises a structure that defines a plurality of holes extending inwardly from the second surface toward the base, wherein the holes are arranged in a micropattern, wherein the base and the stent are coterminous, wherein the base covers the apertures of the stent.

Statement 2. The endoprosthesis of statement 1, wherein when the endoprosthesis expands in a lumen defined by a vessel wall, the structure defining a plurality of holes arranged in a micropattern applies a force that creates a desired interlock between the vessel wall and the endoprosthesis.

Statement 3. The endoprosthesis of statement 1 or statement 2, wherein shape of the plurality of holes is selected from the group consisting of a cylinder, a rectangular prism, a prism with a polygonal base, a sphere, and an ellipsoid.

Statement 4. The endoprosthesis of any of statements 1-3, wherein the plurality of holes of the micropattern are cylindrical microholes, each cylindrical microhole having a diameter and a height.

Statement 5. The endoprosthesis of statement 4, wherein the diameter is between about 1 µm and 100 µm.

Statement 6. The endoprosthesis of statement 5, wherein the diameter is between about 14 µm and 18 µm.

Statement 7. The endoprosthesis of statement 4, wherein the height is between about 1 µm and 100 µm.

Statement 8. The endoprosthesis of statement 7, wherein the height is between about 14 µm and 18 µm.

Statement 9. The endoprosthesis of statement 4, wherein the diameter of the cylindrical microhole is equal to the height of the cylindrical microhole.

Statement 10. The endoprosthesis of statement 4, wherein each cylindrical microhole has a lateral surface, wherein the lateral surface of the cylindrical microhole is separated from the lateral surfaces of an adjacent microhole by a distance greater than the diameter of the cylindrical microhole.

Statement 11. The endoprosthesis of statement 1, wherein each hole of the micropattern has a first dimension and a second dimension, wherein the first dimension is between about 1 µm and 100 µm, wherein the second dimension is between about 1 µm and 100 µm, and wherein a ratio between the first dimension and the second dimension is between about 1 and 1.3.

Statement 12. The endoprosthesis of any of statements 1-11, wherein the micropattern is a grid pattern.

Statement 13. The endoprosthesis of any of statements 1-12, wherein the polymeric coating is a polymeric material selected from the group consisting of hydrogels and silicones.

Statement 14. The endoprosthesis of any of statements 1-13, wherein the holes of the micropattern are uniform.

Statement 15. The endoprosthesis of any of statements 1-14, wherein the micropattern includes holes of a first configuration and holes of at least a second configuration.

Statement 16. The endoprosthesis of any of statements 1-15, wherein the second surface defines a plurality of openings from which the holes extend.

Statement 17. The endoprosthesis of statement 16 wherein the plurality of openings comprises a first opening and a second opening and the plurality of holes comprises at least a first hole extending from the first opening and a second hole extending from the second opening, wherein the first hole and second hole are in fluid communication via a channel disposed between the first surface and the second surface.

Statement 18. The endoprosthesis of any of statements 1-17, wherein the structure comprises a plurality of intertwining fibers.

Statement 19. The endoprosthesis of any of statements 1-18, wherein the structure is adapted to allow controlled cell ingrowth at an implantation site and allow atraumatic endoprosthesis removal from the implantation site after cell ingrowth occurs.

Statement 20. The endoprosthesis of any of statements 1-19, wherein the first surface defines a length and a width of the coating and wherein the second surface of the coating extends around the plurality of holes continuously along at least one of the length and width of the coating.

Statement 21. A method of manufacturing an endoprosthesis comprising:
forming a polymeric coating, wherein the polymeric coating comprises
a base comprising a first surface; and
a tissue engagement portion comprising a second surface facing away from the first surface, the tissue engagement portion comprises a structure that defines a plurality of holes extending inwardly from the second surface toward the base, wherein the holes are arranged in a micropattern; and
attaching the base of the polymeric coating to an outer surface of a stent, the stent comprising an inner surface defining a lumen.

Statement 22. The method of statement 21, wherein the polymeric coating is formed using a mold having an inverse of the micropattern and injecting a polymeric material into the mold.

Statement 23. The method of statement 21 or statement 22, wherein attaching the base of the polymeric coating to the outer surface of the stent comprises applying an adhesive layer to at least one of the first surface of the base and the outer surface of the stent.

Statement 24. The method of any of statements 21-23, wherein the polymeric coating is formed in a strip and helically wrapped about the outer surface of the stent.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the present disclosure such that the present disclosure should be recognized as also specifically directed to other embodiments having any other possible combination of the features of the dependent claims.

This completes the description of the preferred and alternate embodiments of the present disclosure. Those skilled in the art may recognize other equivalents to the specific embodiment described herein which equivalents are intended to be encompassed by the claims attached hereto.

The invention claimed is:

1. An endoprosthesis having an expanded state and an unexpanded state, the endoprosthesis comprising:
a stent, wherein the stent has an inner surface defining a lumen, an outer surface, a first end, a second end, and a stent thickness defined between the inner surface and the outer surface, wherein the stent defines a plurality of apertures extending through the stent thickness; and
a polymeric coating surrounding the stent and covering at least some of the apertures, the polymeric coating including a surface facing outwardly from the stent, the polymeric coating including a structure that defines a plurality of openings in the surface defining a plurality of holes extending inwardly from the surface toward the stent, the holes configured to allow tissue ingrowth from the surface into the holes upon initial implantation of the endoprosthesis in a body lumen, wherein the holes are arranged in a micropattern, wherein the surface extends continuously around an entire perimeter of each of the plurality of holes.

2. The endoprosthesis of claim 1, wherein the polymeric coating and the stent are coterminous.

3. The endoprosthesis of claim 1, wherein at least some of the plurality of holes extend entirely through the polymeric coating.

4. The endoprosthesis of claim 1, where at least some of the plurality of holes are blind holes.

5. The endoprosthesis of claim 1, wherein the polymeric coating includes a base attached to the outer surface of the stent.

6. The endoprosthesis of claim 1, wherein the plurality of holes have a diameter and a height, wherein a ratio of the height to the diameter is between 1 to 1.3.

7. The endoprosthesis of claim 1, wherein the plurality of holes have a diameter and a spacing between adjacent holes, wherein a ratio of the spacing to the diameter is between 1.01 to 2.0.

8. The endoprosthesis of claim 1, wherein the plurality of holes are arranged in a rectangular array.

9. The endoprosthesis of claim 1, wherein the shape of the plurality of holes is selected from the group consisting of a cylinder, a rectangular prism, a prism with a polygonal base, a sphere, and an ellipsoid.

10. The endoprosthesis of claim 1, wherein the polymeric coating is a polymeric material selected from the group consisting of hydrogels and silicones.

11. The endoprosthesis of claim 1, wherein the polymeric coating at least partially covers the inner surface of the stent.

12. The endoprosthesis of claim 1, wherein the polymeric coating further comprises a plurality of micropillars extending outwardly from the surface.

13. The endoprosthesis of claim 1, wherein each of the plurality of holes has a side surface extending around the entire perimeter of the hole, the side surface extending from the outwardly facing surface of the coating to a base of the hole.

\* \* \* \* \*